(12) United States Patent
Collins et al.

(10) Patent No.: US 10,842,874 B2
(45) Date of Patent: Nov. 24, 2020

(54) SENSITIZATION OF BACTERIAL CELLS TO QUINOLONE ANTIBIOTICS

(71) Applicant: Massachusetts Institute of Technology, Cambridge, MA (US)

(72) Inventors: James J. Collins, Newton, MA (US); Michael Andrew Lobritz, Basel (CH); Arnaud Gutierrez, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/168,628

(22) Filed: Oct. 23, 2018

(65) Prior Publication Data
US 2019/0201532 A1   Jul. 4, 2019

Related U.S. Application Data

(60) Provisional application No. 62/595,648, filed on Dec. 7, 2017.

(51) Int. Cl.
| | |
|---|---|
| *A61K 47/26* | (2006.01) |
| *A61K 31/194* | (2006.01) |
| *A61K 31/496* | (2006.01) |
| *A61K 33/00* | (2006.01) |
| *A61K 45/06* | (2006.01) |
| *A61K 47/02* | (2006.01) |
| *A61K 47/12* | (2006.01) |
| *A61P 31/04* | (2006.01) |
| *A61K 31/4709* | (2006.01) |
| *A61K 31/4741* | (2006.01) |
| *A61K 31/4745* | (2006.01) |
| *A61K 31/5383* | (2006.01) |
| *A61K 31/7004* | (2006.01) |

(52) U.S. Cl.
CPC ............ *A61K 47/26* (2013.01); *A61K 31/194* (2013.01); *A61K 31/4709* (2013.01); *A61K 31/4741* (2013.01); *A61K 31/4745* (2013.01); *A61K 31/496* (2013.01); *A61K 31/5383* (2013.01); *A61K 31/7004* (2013.01); *A61K 33/00* (2013.01); *A61K 45/06* (2013.01); *A61K 47/02* (2013.01); *A61K 47/12* (2013.01); *A61P 31/04* (2018.01)

(58) Field of Classification Search
CPC .. A61K 47/26; A61K 31/194; A61K 31/4709; A61K 31/4741; A61K 31/4745; A61K 31/496; A61K 31/5383; A61K 31/7004; A61K 33/00; A61K 45/06; A61K 47/02; A61K 47/12; A61P 31/04
USPC .................................................... 514/230.2
See application file for complete search history.

(56) References Cited

U.S. PATENT DOCUMENTS

| 2011/0319502 A1* | 12/2011 | Coffey .................. A61K 9/0048 514/777 |
| 2015/0132382 A1* | 5/2015 | Dedhiya ............... A61K 31/665 424/482 |

FOREIGN PATENT DOCUMENTS

| CN | 104524556 A | 4/2015 |
| CN | 105769756 A | 7/2016 |
| CN | 106509457 A | 3/2017 |
| UA | 52816 U | 9/2010 |
| WO | WO 2012/151474 A2 | 11/2012 |
| WO | WO 2015/031765 A2 | 3/2015 |

OTHER PUBLICATIONS

Van Stroe-Biezen et al., Analytica Chimica Acta, 1993, 280, 217-222 (Year: 1993).*
Translation of CN 105769756 (Year: 2016).*
WPI Database Accession No. 2001-135667. Nov. 10, 2000.
WPI Database Accession No. 2016-48318. Mar. 22, 2017.
WPI Database Accession No. 2017-86058. Dec. 8, 2017.
Allison et al., Metabolite-enabled eradictation of bacterial persisters by aminoglycosides.Nature.2011;473:216.
Amato et al., Metabolic control of persister formation in *Escherichia coli*.Mol Cell.2013;50:475.
Asuquo et al., Accumulation and killing kinetics of fifteen quinolones for *Escherichia coli*, *Staphylococcus aureus* and *Pseudomonas aeruginosa*.J Antimicrob Chemother.1999;31:865-880.
Balaban et al., A problem of persistence:still more questions than answers?Nat Rev Microbiol.2013;11:587-591.
Barraud et al., Mannitol enhances antibiotic sensitivity of persister bacteria in Pseudomonas aeruginosa biofilms.PLoS One. 2013;8:e84220.
Berge et al., Pharmaceutical salts. J Pharm Sci. Jan. 1977;66(1):1-19.
Brauner et al., Distinguishing between resistance, tolerance and persistence to antibiotic treatment.Nat Rev Microbiol.2016;14:320-3330.

(Continued)

*Primary Examiner* — Yevgeny Valenrod
(74) *Attorney, Agent, or Firm* — Wolf, Greenfield & Sacks, P.C.

(57) ABSTRACT

Provided herein are pharmaceutical compositions and kits useful for sensitizing a microorganism or a population of microorganisms to a quinolone antibiotic. In a particular aspect, a carbon source and an electron acceptor can sensitize an antibiotic persistent microorganism to treatment with a fluoroquinolone antibiotic. Methods for sensitizing a microorganism to a quinolone antibiotic, reducing the density-dependent persistence (DDP) of an antibiotic resistant microorganism, and reducing the number of persistent cells in a population are also provided. Theses compositions and methods are useful in treating infections resulting from high-density bacterial cultures, such as pneumonia, genitourinary infections, biofilms, prosthetic graft infections, sepsis, and endovascular infections.

23 Claims, 7 Drawing Sheets

Specification includes a Sequence Listing.

(56) References Cited

OTHER PUBLICATIONS

Bush et al., Tackling antibiotic resistance. Nat Rev Microbiol. Nov. 2, 2011;9(12):894-6. doi:10.1038/nrmicro2693.
Caspi et al., The MetaCyc database of metabolic pathways and enzymes and the BioCyc collection of pathway/genome databases. Nucleic Acids Res.2016;44:D471.
Conlon et al., Persister formation in *Staphylococcus aureus* is associated with ATP depletion. Nat Microbiol. 2016;1:1-7.
Dorr et al., Ciprofloxacin causes persister formation by inducing the TisB toxin in *Escherichia coli*.PLoS Biol. 2010;8:e1000317.
Dorr et al., SOS response induces persistence to fluoroquinolones in *Escherichia coli*.PLoS Genet. 2009;5:e1000760.
Drlica et al., Quinolone-medicated bacterial death.Antimicrob Agents Chemother. 2008;52:385.
Dwyer et al., Antibiotics induce redox-related physiological alterations as part of their lethality.Proc Natl Acad Sci USA. 2014;111:E2100.
Fauvart et al., Role of persister cells in chronic infections: clinical relevance and perspectives on anti-persister therapies.J Med Microbiol. 2011;60:699.
Fuchs et al., Anaerobic gene expression in *Staphylococcus aureus*.J Bacteriol. 2007;189:4275.
Grant et al., Eradication of bacterial persisters with antibiotic-generated hydroxyl radicals.Proc Natl Acad Sci USA. 2012;109:12147.
Gutierrez et al., Understanding and Sensitizing Density-Dependent Persistence to Quinolone Antibiotics. Mol Cell. Dec. 21, 2017;68(6):1147-1154.e3. doi:10.1016/j.molcel.2017.11.012. Epub Dec. 7, 2017.
Gutierrez-Estrada et al., Role of chaperones and ATP synthase in DNA gyrade reactivation in *Escherichia coli* stationary-phase cells after nutrient addition. SpringerPlus. 2014;3:656.
Harms et al., Mechanisms of bacterial persistence during stress and antibiotic exposure. Science. 2016;354:1390.
Kim et al., Fumarate-Mediated Persistence of *Escherichia coli* against Antibiotics. Antimicrob Agents Chemother. Mar. 25, 2016;60(4):2232-40. doi: 10.1128/AAC.01794-15. Print Apr. 2016.
Knudsen et al., Survival of bactericidal antibiotic treatment by a persister subpopulation of Listeria monocytogenes.Appl Environ Microbiol. 2013;79:7390.
Laureti et al., Bacterial Responses and Genome Instability Induced by Subinhibitory Concentrations of Antibiotics. Antibiotics (Basel). Mar. 14, 2013;2(1):100-14. doi: 10.3390/antibiotics2010100.
Levin-Reisman et al., Antibiotic tolerance facilitates the evolution of resistance. Science. Feb. 4, 2017;355(6327):826-830. doi: 10.1126/science.aaj2191. Epub Feb 9. 2017.
Levin-Reisman et al., Quantitative Measurements of Type I and Type II Persisters Using ScanLag. Methods Mol Biol. 2016;1333:75-81. doi: 10.1007/978-1-4939-2854-5_7.
Levy et al., Single-nucleotide polymorphism mutation spectra and resistance to quinoloness in *Salmonella enterica* serovar Enteritidis with a mutator phenotype.Antimicrob Agents Chemother. 2004;48:2355-2363.
Lewin et al., The mode of action of quinolones: the paradox in activity of low and high concentrations and activity in the anaerobic environment. Eur J Clin Microbiol Infect Dis. Apr. 1991;10(4):240-8.
Lobritz et al., Antibiotic efficacy is linked to bacterial cellular respiration.Proc Natl Acad Sci USA.2015;112:8173-8180.
Losen et al., Effect of oxygen limitation and medium composition of *Escherichia coli* fermentation in shake-flask cultures. Biotechnol Prog. 2004;20:1062-8.
Maisonneuve et al., (p)ppGpp controls bacterial persistence by stochastic induction of toxin-antitoxin activity.Cell.2013;154:1140 doi: 10.1016/j.cell.2013.07.048. Retraction in: Cell. Feb. 22, 2018;172(5):1135.
Mathieu et al., Discovery and Function of a General Core Hormetic Stress Response in *E. coli* Induced by Sublethal Concentrations of Antibiotics. Cell Rep. Sep. 27, 2016;17(1):46-57. doi: 10.1016/j.celrep.2016.09.001.
Meylan et al., Carbon Sources Tune Antibiotic Susceptibility in Pseudomonas aeruginosa via Tricarboxylic Acid Cycle Control. Cell Chem Biol. Feb. 16, 2017;24(2):195-206. doi: 10.1016/j.chembiol.2016.12.015. Epub Jan. 19, 2017.
Moyed et al., hipA, a newly recognized gene of *Escherichia coli* K-12 that affects frequency of persistence after inhibition of murein synthesis. J Bacteriol. Aug. 1983;155(2):768-75.
Nguyen et al., Active starvation responses mediate antibiotic tolerance in biofilms and nutrient-limited bacteria. Science. Nov. 18, 2011;334(6058):982-6. doi: 10.1126/science.1211037.
Paul et al., rRNA transcription in *Escherichia coli*. Annu Rev Genet. 2004;38:749-70.
Peng et al., Exogenous alanine and/or glucose plus kanamycin kills antibiotic-resistant bacteria. Cell Metab. Feb. 3, 2015;21(2):249-262. doi: 10.1016/j.cmet.2015.01.008.
Portnoy et al., Aerobic fermentation of D-glucose by an evolved cytochrome oxidase-deficient *Escherichia coli* strain. Appl Environ Microbiol. Dec. 2008;74(24):7561-9. doi: 10.1128/AEM.00880-08. Epub Oct. 24, 2008.
Prax et al., Glucose Augments Killing Efficiency of Daptomycin Challenged *Staphylococcus aureus* Persisters. PLoS One. Mar. 9, 2016;11(3):e0150907. doi: 10.1371/journal.pone.0150907. eCollection 2016.
Sezonov et al., *Escherichia coli* physiology in Luria-Bertani broth. J Bacteriol. Dec. 2007;189(23):8746-9. Epub Sep. 28, 2007.
Shan et al., ATP-Dependent Persister Formation in *Escherichia coli*. MBio. Feb. 7, 2017;8(1). pii: e02267-16. doi: 10.1128/mBio.02267-16.
Smith et al., Combating bacteria and drug resistance by inhibiting mechanisms of persistence and adaptation. Nat Chem Biol. Sep. 2007;3(9):549-56.
Tseng et al., Effect of microaerophilic cell growth conditions on expression of the aerobic (cyoABCDE and cydAB) and anaerobic (narGHJI, frdABCD, and dmsABC) respiratory pathway genes in *Escherichia coli*. J Bacteriol. Feb. 1996;178(4):1094-8.
Van Den Bergh et al. Formation, physiology, ecology, evolution and clinical importance of bacterial persisters. FEMS Microbiol Rev. May 1, 2017;41(3):219-251. doi: 10.1093/femsre/fux001.
Zeiler, Evalution of the in vitro bactericidal action of ciprofloxacin on cells of *Escherichia coli* in the logarithmic and stationary phases of growth. Antimicrob Agents Chemother. Oct. 1985;28(4):524-7.
Dwyer et al., Unraveling the physiological complexities of antibiotic lethality. Annu Rev Pharmacol Toxicol. 2015;55:313-32. doi: 10.1146/annurev-pharmtox-010814-124712. Epub Sep. 10, 2014.
PCT/US2018/057042, dated Mar. 11, 2019, International Search Report and Written Opinion.

\* cited by examiner

SENSITIZATION OF BACTERIAL CELLS TO QUINOLONE ANTIBIOTICS

RELATED APPLICATION

The present application claims priority under 35 U.S.C. § 119(e) to U.S. provisional application U.S. Ser. No. 62/595,648, filed Dec. 7, 2017, which is incorporated herein by reference.

GOVERNMENT SUPPORT

This invention was made with Government support under Grant No. HDTRA1-15-1-0051 awarded by the Defense Threat Reduction Agency. The Government has certain rights in the invention.

BACKGROUND OF THE INVENTION

Antibiotics are the main tools to treat infectious diseases caused by bacteria; however, effective therapy is limited by the ability of bacterial populations to escape lethal drug challenges. The evasion of antibiotic stress by bacteria is receiving extensive attention by the scientific community (Van den Bergh et al., 2017). In particular, characterizing and classifying the causes of antibiotic failure has been a recent focus (Brauner et al., 2016). These distinct causes of antibiotic failure include: antibiotic resistance, characterized by a change in the minimal inhibitory concentration; antibiotic tolerance, characterized by a change in killing kinetics; and antibiotic persistence, characterized by the presence of a time dependent bi-phasic killing profile. Bacterial resistance conferred by genetically encoded factors such as efflux pumps, drug-inactivating enzymes, or drug-target mutations is generally well understood, while the latter processes remain poorly characterized (Balaban et al., 2013; Bush et al., 2011). Antibiotic treatment failure associated with bacterial tolerance and persistence is relevant to many infection types, including prosthetic implant-related infections caused by *Staphylococcus aureus* or pulmonary infections caused by *Mycobacterium tuberculosis* (Fauvart et al., 2011). Importantly, drug tolerance and persistence have been identified as physiologic states that can promote the development of genetic resistance (Levin-Reisman et al., 2017), further underscoring the need to understand the biological basis for these phenomena.

Many early investigations into phenotypic tolerance and persistence found links to intrinsic genetic factors, including toxin-antitoxin modules and stress response regulators (Dorr et al., 2010; Moyed and Bertrand, 1983). However, none of these factors could fully account for the variety and magnitude of observed phenotypes. More recently, stress responses related to extrinsic environmental cues, such as the starvation-induced stringent response (SOS), have been identified as drivers of antibiotic treatment failure (Dorr et al., 2009; Maisonneuve et al., 2013). This concept suggests the importance of the bacterial growth environment as a modulating factor of antibiotic efficacy (Harms et al., 2016). Consistent with this, attempts to potentiate aminoglycoside activity have focused on metabolic stimulation (Allison et al., 2011; Barraud et al., 2013; Knudsen et al., 2013; Meylan et al., 2017; Peng et al., 2015).

There is an urgent need for effective therapies for antibiotic persistent organisms, such as those associated with high-density growth conditions, e.g., biofilms, prosthetic graft infections, endovascular infections, genitourinary infections (e.g., urinary tract infections), and pneumonias.

SUMMARY OF THE INVENTION

Density-dependent drug failure is a form of antibiotic persistence hallmarked by the reduction of drug efficacy when challenging high cell-density populations. While persister cells are often characterized using killing as a function of the drug incubation time, we define density-dependent persistence (DDP) as dose-dependent reduction in drug efficacy as a function of the initial cell density. To assess mechanisms of DDP, antibiotics from the quinolone family, which are known to be affected by the density of the cell population (Zeiler, 1985), were studied. Quinolone-induced lethality derives from poisoning of the type II topoisomerases, DNA gyrase, and topoisomerase IV, which is proposed to drive DNA fragmentation leading to cell death (Drlica et al., 2008). Though binding and corruption of type II topoisomerases are essential for quinolone-induced bacterial cell death, additional factors, such as by-products of cellular respiration and metabolism have been implicated in the bactericidal properties of quinolones (Dwyer et al., 2014; Dwyer et al., 2015). Underscoring the metabolic element of drug efficacy, the modulation of quinolone antibiotic activity against both *Escherichia coli* and *S. aureus* has been linked to the ability of cells to produce ATP (Conlon et al., 2016; Shan et al., 2017). Here, we show that metabolite exhaustion is a driver in quinolone DDP and provide a strategy to sensitize metabolically limited, high-density cultures of bacteria to quinolones. This approach may have broad applicability to non-dividing bacterial infections and significantly impact the utility of quinolone antibiotics in the treatment of clinical bacterial infections.

Thus, in some aspects, the invention provides compositions, methods, kits, and strategies useful for sensitizing a microorganism to an antibiotic. In some aspects, the invention provides compositions, methods, kits, and strategies useful for sensitizing a microorganism (e.g., bacteria) to a quinolone antibiotic. In some aspects, the invention provides compositions and methods useful for preventing or reducing the density-dependent persistence (DDP) of a microorganism. In some embodiments, the microorganism population is characterized by high-density growth. In some aspects, the compositions and methods provided herein are useful in preventing, reducing, or eliminating persister cells in a population of microorganisms. Without wishing to be bound by any particular theory, a persister cell is a dormant variant (e.g., slow-growing or growth-arrested) of a regular cell that may form randomly in a population of microorganisms. Persister cells are highly tolerant to antibiotics, including, e.g., quinolone antibiotics, the "gold standard" antibiotic used as first-line therapy against many bacterial infections including biofilms, prosthetic graft infections, endovascular infections, genitourinary infections (e.g., urinary tract infections), and pneumonias. Thus, provided herein are compositions, methods, kits, and strategies useful in treating an infection comprising one or more persister cells in a population of microorganisms. In some aspects, provided herein are compositions comprising a carbon source and an electron acceptor in combination with a quinolone antibiotic useful in preventing or treating an infection in a subject in need thereof. The infection may be comprised of a population of microorganisms wherein one or more persister cells are present.

In some aspects, the invention makes use of a carbon source in combination with an electron acceptor. In some embodiments, a pharmaceutical composition comprises a carbon source and an electron acceptor. In some embodiments, the carbon source is an intermediate in glycolysis. In some embodiments, the carbon source is a pyranose sugar. In some embodiments, the carbon source is a furanose sugar. In some embodiments, the carbon source is glucose. In some embodiments, the electron acceptor is fumarate, or a salt thereof. In some embodiments, the electron acceptor is oxygen.

In some aspects, the invention makes use of a carbon source (e.g., glucose), an electron acceptor (e.g., fumarate), and an antibiotic (e.g., quinoline). In some embodiments, a pharmaceutical composition comprises a carbon source, an electron acceptor, and a quinolone antibiotic. In some embodiments, the quinolone antibiotic is flumequine, oxolinic acid, or rosoxacin. In some embodiments, the quinolone antibiotic is a fluoroquinolone. In some embodiments, the fluoroquinolone is ciprofloxacin, levofloxacin, moxifloxacin, garenoxacin, gatifloxacin, gemifloxacin, fleroxacin, lomefloxacin, nadifloxacin, norfloxacin, ofloxacin, pefloxacin, rufloxacin, balofloxacin, grepafloxacin, pazufloxacin, sparfloxacin, temafloxacin, tosufloxacin, clinafloxacin, sitafloxacin, prulifloxacin, trovalfloxacin, delafloxacin, or ozenoxacin. In some embodiments, the fluoroquinolone is ciprofloxacin. In some embodiments, the fluoroquinolone is levofloxacin. In some embodiments, the fluoroquinolone is moxifloxacin.

In one aspect, provided herein are pharmaceutical compositions comprising a carbon source and an electron acceptor. In some embodiments, the pharmaceutical composition comprises a carbon source and fumarate. In some embodiments, the pharmaceutical composition comprises a carbon source and oxygen. In some embodiments, the pharmaceutical composition comprises glucose and fumarate. In some embodiments, the pharmaceutical composition comprises glucose and oxygen.

In another aspect, provided herein are pharmaceutical compositions comprising a quinolone antibiotic, a carbon source, and an electron acceptor.

In some embodiments, one or more agents in the pharmaceutical composition (e.g., carbon source, electron acceptor, quinolone antibiotic) is formulated for enteral administration. In some embodiments, one or more agents in the pharmaceutical composition is formulated for parenteral administration (e.g., intravenous). In some embodiments, one or more agents in the pharmaceutical composition is formulated for administration via a pulmonary route (e.g., inhalation). In some embodiments, one or more agents in the pharmaceutical composition is formulated for local administration. In some embodiments, one or more agents in the pharmaceutical composition is formulated for topical administration. In some embodiments, one or more agents in the pharmaceutical composition is encapsulated in a nanoparticle, micelle, or liposome for delivery and/or administration.

In another aspect, described herein is a method for sensitizing a microorganism to a quinolone antibiotic. In some embodiments, method comprises (i) contacting the microorganism with an effective amount of a carbon source; and (ii) contacting the microorganism with an effective amount of an electron acceptor.

In yet another aspect, described herein is a method for preventing or reducing the density-dependent persistence (DDP) of a microorganism. In some embodiments, the method comprises contacting a population of microorganisms comprised of one or more antibiotic persister cells with (i) an effective amount of a carbon source, and (ii) an effective amount of an electron acceptor.

In yet another aspect, described herein is a method for preventing, reducing, or eliminating persister cells in a population of microorganisms. In some embodiments, the method comprises (i) contacting the cells with an effective amount of a carbon source, (ii) contacting the cells with an effective amount of an electron acceptor, and (iii) contacting the cells with an effective amount of a quinolone antibiotic.

In yet another aspect, described herein is a method for preventing or treating an infection in a subject in need thereof, wherein the infection is comprised of a population of microorganisms comprising one or more persister cells. In some embodiments, the method comprises (i) administering to the subject an effective amount of a carbon source, (ii) administering to the subject an effective amount of an electron acceptor, and (iii) administering to the subject an effective amount of a quinolone antibiotic.

In some embodiments, the carbon source, electron acceptor, and/or quinolone antibiotic are administered enterally to a subject in need thereof. In some embodiments, the carbon source, electron acceptor, and/or quinolone antibiotic are administered intravenously to a subject in need thereof. In some embodiments, the carbon source, electron acceptor, and/or quinolone antibiotic are administered locally (e.g., topically) to a subject in need thereof. In some embodiments, the carbon source, electron acceptor, and/or quinolone antibiotic are administered to a subject in need thereof via a pulmonary route (e.g., inhalation). In some embodiments, the carbon source and electron acceptor are administered via a pulmonary route in combination with a quinolone antibiotic administered via an enteral or parenteral route. In some embodiments, the carbon source and electron acceptor are administered enterally in combination with a quinolone antibiotic administered via an enteral or parenteral route.

Also provided herein are kits comprising a pharmaceutical composition described herein. The kits may be useful for practicing the methods described herein.

The practice of certain aspects of the present invention may employ conventional techniques of molecular biology, cell culture, recombinant nucleic acid (e.g., DNA) technology, immunology, transgenic biology, microbiology, nucleic acid and polypeptide synthesis, detection, manipulation, and quantification, that are within the ordinary skill of the art. See, e.g., Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., edition as of December 2012; Sambrook, Russell, and Sambrook, *Molecular Cloning: A Laboratory Manual*, $3^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988. Information regarding diagnosis and treatments of various infections is found in Longo, D., et al. (eds.), Harrison's Principles of Internal Medicine, $19^{th}$ Edition; McGraw-Hill Professional, 2015. Information regarding various therapeutic agents and human diseases, including bacterial infections and quinolone antibiotics, is found in Brunton, L., et al. (eds.) Goodman and Gilman's The Pharmacological Basis of Therapeutics, $13^{th}$ Ed., McGraw Hill, 2017. All patents, patent applications, books, articles, documents, databases, websites, publications, references, etc., mentioned herein are incorporated by reference in their entirety. In case of a conflict between the specification and any of the incorporated references, the specification (including any amendments thereof), shall control. Applicants reserve the right to amend the specification based, e.g., on any of the incorporated material and/or to correct obvious errors. None of the content of the incorporated material shall limit the invention. Standard art-accepted meanings of terms are used herein unless indicated otherwise. Standard abbreviations for various terms are used herein.

BRIEF DESCRIPTION OF THE DRAWINGS

(FIG. 1A) *E. coli* growth in LB medium over time (mean±SEM n=7); dashed lines represent the cell density sampling—lower=1%, middle=10%, and upper=100% of the maximum density. (FIG. 1B) Ciprofloxacin dose response of *E. coli* (mean±SEM n=3) from culture at different cell density—white squares 1%, black squares 10%, and gray squares 100% of the maximum density; the dashed line highlights the concentration of 1 µg/ml, which is used in the future sets of experiments. (FIG. 1C) Density-dependent persistence to 1 µg/mL ciprofloxacin. (FIG. 1D) Density-dependent expression of GFP by the $P1_{rrnB}$ promoter. (FIG. 1E) Sensitivity to 1 µg/mL ciprofloxacin of the ppGpp$^0$ mutant in stationary phase culture (mean±SEM, n=3, * Mann-Whitney P<0.05). (FIG. 1F) Density-dependent persistence to 1 µg/mL ciprofloxacin of the ppGpp$^0$ mutant. In (FIG. 1B), (FIG. 1C) and (FIG. 1F), $10^{2*}$ shows our limit of detection. In (FIG. 1C), (FIG. 1D), and (FIG. 1F), each symbol represents a different biological replicate.

(FIG. 2A) Glucose-dependent sensitization to 1 µg/mL of ciprofloxacin in stationary phase shaking (light bar) or static (dark bar) culture (mean±SEM, n=3). (FIG. 2B) Dissolved oxygen concentration (left axis) compared with growth in *E. coli* static culture (right axis mean±SEM, n=5). (FIG. 2C) Density-dependent persistence to ciprofloxacin in *E. coli* static culture. (FIG. 2D) Expression of the frdA and cyoA mRNA compared to the reference zwf in static culture (mean±SEM, n=3). (FIG. 2E) Aeration-dependent sensitization of *E. coli* static culture by glucose to 1 µg/mL of ciprofloxacin (mean±SEM, n=4). (FIG. 2F) Expression of the frdA and cyoA mRNA compared to the reference zwf in shaked culture (mean±SEM, n=3). In (FIG. 2A), (FIG. 2E) and (FIG. 2C), $10^{-4*}$ and $10^{2*}$ shows our limit of detection. In (FIG. 2B) and (FIG. 2C), each symbol represents a different biological replicate. In (FIG. 2D) and (FIG. 2F), * unpaired t-test comparison to the 120 min time point P<0.05.

(FIG. 3A) Alternative electron acceptors synergize glucose sensitization to 1 µg/mL of ciprofloxacin in shacked MOPS stationary phase culture. (FIG. 3B) Glucose-fumarate (0.2%-0.2%) synergy across ciprofloxacin concentration in shacked MOPS stationary phase culture. (FIG. 3C) Glucose-fumarate (0.2%-0.2%) synergy across ciprofloxacin concentration in shacked LB stationary phase culture. (FIG. 3D) The glucose-fumarate synergy depends on the fumarate reductase activity. In (FIG. 3A), (FIG. 3B), (FIG. 3C) and (FIG. 3D), data represent the mean±SEM, n=3, of the percent survival compared to ciprofloxacin untreated; $10^{-4*}$ shows our limit of detection. (FIG. 3E), (FIG. 3F). Glucose-fumarate sensitization to different concentrations of gentamicin (FIG. 3E) and ampicillin (FIG. 3F) (mean±SEM, n=3); $10^{2*}$ shows our limit of detection.

(FIG. 4A) and (FIG. 4B) Density-dependent persistence to ciprofloxacin in *M. smegmatis* (FIG. 4A) and *S. aureus* (FIG. 4B); dark circles correspond to stationary phase cells and squares correspond to cells treated at 1% maximal density; $10^{2*}$ shows our limit of detection. (FIG. 4C) Glucose-fumarate sensitization of shacked stationary phase *M. smegmatis* culture to ciprofloxacin. (FIG. 4D) Aeration-dependent glucose sensitization of static stationary phase *S. aureus*. $10^{-4*}$ shows our limit of detection. (FIG. 4A) and (FIG. 4B) show mean±SEM, n=3; (FIG. 4C) and (FIG. 4D) show mean±SEM, n=3 of percent survival compare to ciprofloxacin untreated.

(FIG. 5A) *E. coli* growth in MOPS medium over time (mean±SEM n=7); dashed lines represent the cell density sampling—lower 1%, middle 10%, and upper 100% of the maximum density. (FIG. 5B) Ciprofloxacinfloxacin dose response of *E. coli* in MOPS (mean±SEM n=3) from cultures at different cell density—lower 1%, middle 10%, and upper 100% of the maximum density; the dashed line highlights the concentration of 1 µg/ml, which is used in the future sets of experiments. (FIG. 5C) Density-dependent persistence to ciprofloxacin in MOPS; each symbol represents a different biological replicate. (FIG. 5D), (FIG. 5E) Dilution effect on persistence; cells were diluted 1/10 to 1/10000 fold from the overnight culture, grown for an hour and treated with 1 µg/mL ciprofloxacin (FIG. 5D) or 10 µg/mL ciprofloxacin (FIG. 5E) for 24 hours (mean±SEM n=3). (FIG. 5F), (FIG. 5G) A comparison of % survival of WT (dark) and ΔrecB (light) cells treated with varying concentrations of ciprofloxacin at 1% maximum density (FIG. 5F) and in stationary phase (FIG. 5G). (FIG. 5H) Measurement of ciprofloxacin uptake in stationary phase as a function of the concentration in the media (mean±SEM n=3). (FIG. 5I) Density-dependent expression of GFP by the $P1_{rrnB}$ promoter in the ppGpp$^0$ mutant; each symbol represents a different biological replicate. In (FIG. 5B), (FIG. 5C), (FIG. 5F) and (FIG. 5G), $10^{2*}$ shows our limit of detection. In (FIG. 5D) and (FIG. 5E), the entire 1 mL of cultures was plated.

(FIG. 6A) Measurement of the aeration dependent ciprofloxacin uptake in MOPS static stationary phase culture with addition of 0.4% glucose (mean±SEM n=3). (FIG. 6B), (FIG. 6C) Aeration-dependent sensitization of *E. coli* WT and ECOM strain stationary culture by glucose to ciprofloxacin 1 µg/mL (FIG. 6B) and 10 µg/mL (FIG. 6C); data represent the mean±SEM, n=3 of the percent survival compared to ciprofloxacin untreated; $10^{-4*}$ shows our limit of detection.

(FIG. 7A) Survival of stationary phase WT cells treated with 1 µg/mL ciprofloxacin at varying concentrations of added glucose and 0.4% added fumarate (light bars) or no fumarate (dark bars). (FIG. 7B) Survival of stationary phase cells treated with 1 µg/mL ciprofloxacin and varying concentrations of added glucose in the ΔfrdA background (light bars) and WT background (dark bars). (FIG. 7C) Growth of cultures treated or not treated with glucose-fumarate (0.2%-0.2%), ns: P>0.05 Mann-Whitney. (FIGS. 7A-7F) show mean±SEM, n=3. (FIG. 7A), (FIG. 7B) and (FIG. 7F) show the percent survival compared to ciprofloxacin untreated;

10-4* shows our limit of detection. (FIG. 7C), (FIG. 7D) and (FIG. 7E) $10^2$* shows our limit of detection.

DEFINITIONS

Figure 1A:
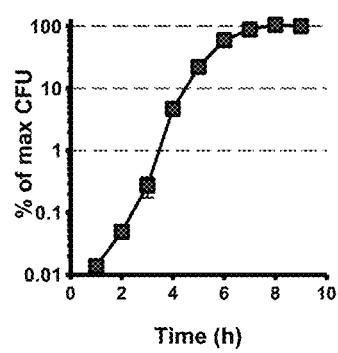
FIGS. 1A-1F. *E. coli* density-dependent persistence to ciprofloxacin.

Descriptions and certain information relating to various terms used in the present disclosure are collected here for convenience.

"Agent" is used herein to refer to any substance, compound (e.g., molecule), supramolecular complex, material, or combination or mixture thereof. A compound may be any agent that can be represented by a chemical formula, chemical structure, or sequence. Example of agents, include, e.g., small molecules, polypeptides, nucleic acids, etc. In general, agents may be obtained using any suitable method known in the art. The ordinary skilled artisan will select an appropriate method based, e.g., on the nature of the agent. An agent may be at least partly purified. In some embodiments an agent may be provided as part of a composition, which may contain, e.g., a counter-ion, aqueous or non-aqueous diluent or carrier, buffer, preservative, or other ingredient, in addition to the agent, in various embodiments. In some embodiments an agent may be provided as a salt, ester, hydrate, or solvate. In some embodiments an agent is cell-permeable, e.g., within the range of typical agents that are taken up by cells and acts intracellularly, e.g., within mammalian cells, to produce a biological effect. Embodiments exhibiting such alternative protonation states, configurations (e.g., geometric or stereoisomeric forms), solvates, and forms are encompassed by the present disclosure where applicable. For example, an "antibiotic agent" refers to any agent that may be useful for treating an infection.

The term "antibiotic" encompasses any antimicrobial agent used in the prevention, reduction, elimination, or treatment of an infection. The infection may be a bacterial infection, or any infection caused by a microbe. In general, antibiotics kill or inhibit the growth of bacterial cells. The antibiotic may also possess antiprotozoal (e.g., for the treatment of parasitic diseases and/or infections) activity. Narrow-spectrum antibiotics target specific types of bacteria, such as gram-negative or gram-positive, whereas broad-spectrum antibiotics affect a wide range of bacteria. Antibiotics are commonly classified based on their mechanism of action, chemical structure, or spectrum of activity. For example, an antibiotic may target and/or inhibit bacterial functions or growth processes. Antibiotics that target the bacterial cell wall (e.g., penicillins and cephalosporins), the cell membrane (e.g., polymyxins), or interfere with essential bacterial enzymes (e.g., rifamycins, lipiarmycins, quinolones, and sulfonamides) have bactericidal activities. Protein synthesis inhibitors (e.g., aminoglycosides, macrolides, lincosamides, and tetracyclines) are usually bacteriostatic (with the exception of bactericidal aminoglycosides). In some embodiments, the antibiotic is an aminoglycoside, quinolone, macrolide, lincosamide, tetracycline, penicillin, cephalosporin, or polymyxin, or a derivative thereof. In some embodiments, the antibiotic is a quinolone, or derivative thereof (e.g., fluoroquinolone).

"Antibiotic persistence" describes the ability of a subpopulation of a clonal bacterial population to survive exposure to high concentrations of an antibiotic. Persistence is typically observed when the majority of the bacterial population is rapidly killed, while a subpopulation (i.e., persister cells) persists for a much longer period of time, despite the population being clonal. The resulting time-kill curve will be bi-phasic, owing to the heterogeneous response of persistent and non-persistent subpopulations. The phrase "density-dependent persistence" refers to the antibiotic persistence exhibited by a microorganism present in a high-density population. As used herein, density-dependent persistence (DDP) characterized as a dose-dependent reduction in drug (e.g., antibiotic) efficacy as a function of initial cell density.

"Antibiotic resistance" describes the inherited ability of a microorganism to grow at high concentrations of an antibiotic, irrespective of the duration of treatment, and is quantified by the minimum inhibitory concentration (MIC) of that antibiotic. In general, a higher MIC is required to kill an antibiotic resistant microorganism.

"Antibiotic tolerance" describes the ability, whether inherited or developed, of a microorganism to survive transient exposure to high concentrations of an antibiotic without a change in the MIC, which is often achieved by slowing down an essential bacterial process.

The term "carbon source" refers to any agent that comprises a carbon atom. A carbon source may be any carbon containing molecule (e.g., carbohydrate, amino acid, fatty acid, $CO_2$) used by an organism for the synthesis of its organic molecules. In some embodiments, the carbon source is a sugar.

The term "electron acceptor" encompasses any agent that can accept an electron or pair of electrons transferred to it from another source. Upon accepting a pair of electrons, the electron acceptor becomes reduced, that is, its oxidation number increases (i.e., an electron acceptor is an oxidizing agent). Examples of electron acceptors include oxygen, nitrate, iron (III), manganese (IV), sulfate, fumarate, and carbon dioxide, among others. In addition, in some microorganisms the chlorinated solvents such as tetrachloroethylene (PCE), trichloroethylene (TCE), dichloroethene (DCE), and vinyl chloride (VC) can serve as electron acceptors. Those of ordinary skill in the art will be able to easily ascertain agents (e.g., small molecules) that can serve as electron acceptors, i.e., an agent that can accept a pair of electrons and become itself reduced in the process. In some embodiments, the electron acceptor is fumarate, or a salt thereof.

An "effective amount" or "effective dose" of an agent (or composition containing such agent) refers to the amount sufficient to achieve a desired biological and/or pharmacological effect, e.g., when delivered to a cell or organism according to a selected administration form, route, and/or schedule. As will be appreciated by those of ordinary skill in this art, the absolute amount of a particular agent or composition that is effective may vary depending on such factors as the desired biological or pharmacological endpoint, the agent to be delivered, the target tissue, etc. Those of ordinary skill in the art will further understand that an "effective amount" may be contacted with cells or administered to a subject in a single dose, or through use of multiple doses, in various embodiments. The term "effective amount" also encompasses a "therapeutically effective amount". A therapeutically effective amount of a pharmaceutical composition described herein is an amount sufficient to provide a therapeutic benefit in the treatment of an infection or to delay or minimize one or more symptoms associated with the infection. A therapeutically effective amount of a pharmaceutical composition means an amount of therapeutic composition, alone or in combination with other therapies, which provides a therapeutic benefit in the treatment of the infection. The term "therapeutically effective amount" can encompass an amount that improves overall therapy, reduces or avoids symptoms, signs, or causes of the infection, and/or enhances the therapeutic efficacy of another therapeutic agent (e.g., an additional antibiotic agent). In certain embodiments, a therapeutically effective amount is an amount sufficient for sensitizing an antibiotic persistent microorganism to a quinolone antibiotic. In certain embodiments, a therapeutically effective amount is an amount sufficient for preventing or reducing the density-dependent persistence (DDP) of a microorganism. In certain embodiments, a therapeutically effective amount is an amount sufficient for preventing, reducing, or eliminating persister cells in a population of microorganisms. In certain embodiments, a therapeutically effective amount is an amount sufficient to prevent an infection, wherein the infection comprises a population of microorganisms comprising one or more persistent cells.

An "infection" refers to an infection with a microorganism. In certain embodiments, the infection is an infection with a bacteria, i.e., a bacterial infection. Various microbial infections include, but are not limited to, skin infections, GI infections, urinary tract infections, genitourinary infections, sepsis, blood infections, pulmonary infections (e.g., pneumonia), and systemic infections. Exemplary bacterial infections include, but are not limited to, infections with a gram positive bacteria (e.g., of the phylum Actinobacteria, phylum Firmicutes, or phylum Tenericutes); gram negative bacteria (e.g., of the phylum Aquificae, phylum Deinococcus-Thermus, phylum Fibrobacteres/Chlorobi/Bacteroidetes (FCB), phylum Fusobacteria, phylum Gemmatimonadest, phylum Ntrospirae, phylum Planctomycetes/Verrucomicrobia/Chlamydiae (PVC), phylum Proteobacteria, phylum Spirochaetes, or phylum Synergistetes); or other bacteria (e.g., of the phylum Acidobacteria, phylum Chlroflexi, phylum Chrystiogenetes, phylum Cyanobacteria, phylum Deferrubacteres, phylum Dictyoglomi, phylum Thermodesulfobacteria, or phylum Thermotogae). In some embodiments, the infection is caused by a gram positive bacterium. In certain embodiments, the bacteria is a member of the phylum Firmicutes and the genus *Staphylococcus*, i.e., the bacterial infection is a *Staphylococcus* infection. Exemplary *Staphylococci* bacteria include, but are not limited to, *S. arlettae, S. aureus, S. auricularis, S. capitis, S. caprae, S. carnous, S. chromogenes, S. cohii, S. condimenti, S. croceolyticus, S. delphini, S. devriesei, S. epidermis, S. equorum, S. felis, S. fluroettii, S. gallinarum, S. haemolyticus, S. hominis, S. hyicus, S. intermedius, S. kloosii, S. leei, S. lenus, S. lugdunesis, S. lutrae, S. lyticans, S. massiliensis, S. microti, S. muscae, S. nepalensis, S. pasteuri, S. penttenkoferi, S. piscifermentans, S. psuedointermedius, S. psudolugdensis, S. pulvereri, S. rostri, S. saccharolyticus, S. saprophyticus, S. schleiferi, S. sciuri, S. simiae, S. simulans, S. stepanovicii, S. succinus, S. vitulinus, S. warneri*, and *S. xylosus*. In certain embodiments, the *Staphylococcus* infection is an *S. aureus* infection. In certain embodiments, the *Staphylococcus* infection is an *S. epidermis* infection. In some embodiments, the gram positive bacterium is a member of the genus *Streptococcus*. In some embodiments, the bacterium is *Mycobacterium smegmatis*. In some embodiments, the infection is caused by a gram negative bacterium. In some embodiments, the bacterium is *Escherichia coli*. In some embodiments, the bacterium is *Pseudomonas aeruginosa*. In some embodiments, the bacterium is *Haemophilus influenzae*. In some embodiments, the infection comprises more than one type of pathogenic microorganism.

The term "microorganism" refers to any single-celled organism. A microorganism may also be present in a colony of cells (e.g., a population of microorganisms). As used herein, the term microorganism may refer to any microorganism in the Archaea or Bacteria domain. In some embodiments, the microorganism is a bacterium. In some embodiments, the population of microorganisms comprises at least one bacterium. In some embodiments, the bacterium is a gram-positive bacterium. In some embodiments, the bacterium is a gram-negative bacterium. In some embodiments, the bacterium is pathogenic (i.e., may cause an infection). A "high-density population" of microorganisms refers to a population of microorganisms wherein the density of microorganisms is at least 10% or higher of the maximum population density.

The terms "persistent cell," "persister cell," and "persistent microorganism" are used interchangeably herein. The term persistent cell also encompasses antibiotic persistent cells. The cells may be persistent to one or more types of antibiotics. In some embodiments, the cells are persistent to quinolone antibiotics. In some embodiments, the cells are persistent to ciprofloxacin. A persister cell can be a Type I or a Type II persister cell. A Type 1 persister is a cell that has been triggered by a stressful environment to differentiate and become antibiotic tolerant using strategies such as starvation to resist death. Type I persisters spawn during the stationary phase of the cell lifecycle and do not increase in number during the growth phase. Type II persisters are slow growing cells that are repetitively produced in the absence of environmental stress or triggers. In some embodiments, a persistent microorganism is a bacterium. In some embodiments, the bacterium is a gram positive bacterium. In some embodiments, the gram positive bacterium is a member of the genus *Staphylococcus* or *Streptococcus*. In some embodiments, the bacterium is *Staphylococcus aureus*. In some embodiments, the bacterium is *Mycobacterium smegmatis*. In some embodiments, the bacterium is a gram negative bacterium. In some embodiments, the bacterium is *Escherichia coli*. In some embodiments, the bacterium is *Pseudomonas aeruginosa*. In some embodiments, the bacterium is *Haemophilus influenzae*. In some embodiments, the persister cell or persistent microorganism is present in vitro. In some embodiments, the persister cell or persistent microorganism is present in vivo.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population. In some embodiments, the subject has had or has been exposed to a microbial infection. In some embodiments, the subject has previously had a bacterial infection.

As used herein, the term "salt" refers to any and all salts, and encompasses pharmaceutically acceptable salts. The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and N+(C1-4 alkyl)4-salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" may be any vertebrate organism in various embodiments. A subject may be individual to whom a pharmaceutical composition is administered, e.g., for experimental, diagnostic, and/or therapeutic purposes, or from whom a sample is obtained or on whom a procedure is performed. In some embodiments a subject is a mammal, e.g. a human, non-human primate, or rodent (e.g., mouse, rat, rabbit). In some embodiments, a subject is a human.

A "sugar" is a molecule comprised of carbon, hydrogen, and oxygen atoms. "Sugar" may be used interchangeably with "carbohydrate". The term "sugar" encompasses monosaccharides (i.e., simple sugars) with the general formula $C_nH_{2n}O_n$. Exemplary monosaccharides include glucose (dextrose), fructose (levulose), and galactose, among others. Monosaccharides are chiral molecules, and thus can exist as either the D- or L-isomeric form. In some embodiments, a sugar can be utilized as a carbon source in a pharmaceutical composition or method described herein. The term sugar also encompasses both the furanose and pyranose forms of a 6-carbon sugar (i.e., a hexose). A furanose sugar is the cyclic, 5-membered ring form of a 6-carbon sugar (hexose), wherein the ring is made up of 4 carbon atoms and one oxygen atom. Exemplary furanose sugars include, e.g., fructose. A pyranose sugar is the cyclic, 6-membered ring form of a 6-carbon sugar (hexose), wherein the ring is made up of five carbon atoms and one oxygen atom. Exemplary pyranose sugars include, e.g., β-D-glucose, D-allose, D-galactose, D-mannose, etc. In some embodiments, the sugar is an intermediate in glycolysis. In some embodiments, the sugar is a furanose sugar. In some embodiments, the sugar is a pyranose sugar. In some embodiments, the sugar is glucose.

"Treat", "treating" and similar terms as used herein in the context of treating a subject refer to providing medical and/or surgical management of a subject. Treatment may include, but is not limited to, administering an agent or composition (e.g., a pharmaceutical composition) to a subject. Treatment is typically undertaken in an effort to alter the course of an infection (which term is used to indicate any disease, disorder, syndrome or undesirable condition warranting or potentially warranting therapy) in a manner beneficial to the subject. The effect of treatment may include reversing, alleviating, reducing severity of, delaying the onset of, curing, inhibiting the progression of, and/or reducing the likelihood of occurrence or recurrence of the infection or one or more symptoms or manifestations of the infection. A pharmaceutical composition may be administered to a subject who has an infection or is at increased risk of developing an infection relative to a member of the general population. For example, a subject who has undergone surgery may be at a higher risk for developing a prosthetic graft infection or pneumonia. In some embodiments, a pharmaceutical composition may be administered to a subject who has had an infection, but no longer shows evidence of the infection. The pharmaceutical composition may be administered e.g., to reduce the likelihood of recurrence of evident infection. A therapeutic agent may be administered prophylactically, i.e., before development of any symptom or manifestation of an infection. "Prophylactic treatment" refers to providing medical and/or surgical management to a subject who has not developed an infection or does not show evidence of an infection in order, e.g., to reduce the likelihood that the infection will occur or to reduce the severity of the infection should it occur. The subject may have been identified as being at risk of developing the infection (e.g., at increased risk relative to the general population or as having a risk factor that increases the likelihood of developing the infection).

The term "quinolone" encompasses any antibiotic with a bicyclic 4-quinolone core structure. Quinolones are broad spectrum antibiotics commonly used in human and verterinary medicine to prevent, reduce, eliminate, or treat bacterial infections. In some embodiments, the quinolone antibiotic is flumequine, oxolinic acid, or rosoxacin. In some embodiments, the quinolone antibiotic is a fluoroquinolone antibiotic. In some embodiments, the fluoroquinolone is ciprofloxacin, levofloxacin, moxifloxacin, garenoxacin, gatifloxacin, gemifloxacin, fleroxacin, lomefloxacin, nadifloxacin, norfloxacin, ofloxacin, pefloxacin, rufloxacin, balofloxacin, grepafloxacin, pazufloxacin, sparfloxacin, temafloxacin, tosufloxacin, clinafloxacin, sitafloxacin, prulifloxacin, trovalfloxacin, delafloxacin, or ozenoxacin. In some embodiments, the fluoroquinolone is ciprofloxacin, levofloxacin, or moxifloxacin. In some embodiments, the fluoroquinolone is ciprofloxacin. In some embodiments, the fluoroquinolone is levofloxacin. In some embodiments, the fluoroquinolone is moxifloxacin.

DETAILED DESCRIPTION OF CERTAIN EMBODIMENTS

Pharmaceutical Compositions

The present disclosure provides the insight that cell killing by quinolone antibiotics sometimes requires the activity of respiratory metabolic pathways, which can be accomplished by a limited number of metabolic inputs. It is known that topoisomerase activity is ATP-dependent, and that stationary phase cells require topoisomerases to recover supercoiling, suggesting that starvation states, which may be encountered by cells growing in high-density population environments (e.g., biofilms, etc.) may limit the activity of these enzymes. These cells, which are often termed "persister" cells, become antibiotic persistent and resistant to treatment with antibiotics, even at high dosages. A multitude of infections which involve high-density microorganism populations, including but not limited to, pneumonias, genitourinary infections, an infection on a foreign body, and infections associated with or characterized by biofilm growth (e.g., cystic fibrosis), are recalcitrant to antibiotic treatment, making persistent infections difficult to prevent or treat. Antibiotic persistent cells are a clinically relevant issue in need of a solution. The compositions and methods provided herein provide the advantage of sensitizing persistent cells within a population of microorganisms (e.g., a high-density population) to quinolone antibiotics, which are the first-line of defense and are generally effective against the majority of cells (e.g., non-persistent cells) that comprise many bacterial infections, and thus provide a treatment option that does not require the arduous development of novel antibiotics. The present disclosure provides, in some aspects, a mechanism for priming respiratory metabolism by the addition of a carbon source and electron acceptor to affect both target corruption and other less-characterized, downstream processes, thereby sensitizing persistent cells to quinolone antibiotics.

Thus, in one aspect, the pharmaceutical composition comprises a carbon source and an electron acceptor. In some embodiments, the carbon source is an intermediate in glycolysis. Intermediates in glycolysis suitable for inclusion in a pharmaceutical composition described herein are, for example, glucose, glucose-6-phosphate, fructose-6-phosphate, fructose-1,6-bisphosphate, glyceraldehyde-3-phosphate, dihydroxyacetone phosphate, 1,3-bisphosphoglycerate, 3-phosphoglycerate, 2-phosphoglycerate, phosphoenolpyruvate, and pyruvate. In some embodiments, the carbon source is a furanose sugar. In some embodiments, the carbon source is a pyranose sugar. In some embodiments, the carbon source is a D-hexose (e.g., glucose). In some embodiments, the carbon source is glucose. In some embodiments, the concentration of glucose in the pharmaceutical compositions is between 0.1-10% (w/v). In some embodiments, the concentration of glucose is between 0.1-5% (w/v). In some embodiments, the concentration of glucose is between 0.1-1% (w/v). In some embodiments, the concentration of glucose is between 0.1-0.5% (w/v). In some embodiments, the concentration of glucose is about 0.4% (w/v). In some embodiments, the concentration of glucose is about 0.2% (w/v).

In biological systems (e.g., cells), an electron acceptor is a compound that receives or accepts an electron or electron pair during cellular respiration or photosynthesis. Cellular respiration is a set of metabolic reactions and processes that take place in the cells of organisms (e.g., microorganisms) to convert biochemical energy from nutrients into adenosine triphosphate (ATP). Depending on the presence of oxygen, an organism can undergo either aerobic respiration (requires $O_2$) or anaerobic respiration in order to create ATP. When cells undergo aerobic respiration, oxygen serves as the terminal electron acceptor, forming water ($H_2O$) with the addition of two protons upon being reduced by electrons used to drive the phosphorylation of ADP to ATP. Thus, in some embodiments, the electron acceptor is oxygen. In some embodiments, the oxygen present in the microorganism's microenvironment or at the site of infection can serve as the electron acceptor. In some embodiments, oxygen is administered directly to the microorganism(s) or directly to the site of infection. In particular, oxygen may be provided directly to the microorganisms via pulmonary administration (e.g., oxygen formulated as an inhalant). In some embodiments, the oxygen provided is pure oxygen gas ($O_2$). In some embodiments, the pharmaceutical composition comprises glucose and oxygen. In some embodiments, the glucose is nebulized in an $O_2$ enriched composition for pulmonary administration. In some embodiments, the glucose is nebulized in pure $O_2$ for pulmonary administration.

As shown in Example 1, high-density populations of microorganisms are less susceptible to treatment with a quinolone antibiotic due to reduced oxygen availability. Thus, a low oxygen level is a factor that limits persister cell death at high cell density. Example 3 illustrates that in these "anaerobic" growth conditions encountered by microorganisms at high cell density, fumarate can serve as a terminal electron acceptor. In some embodiments, the electron acceptor is fumarate. In some embodiments, the pharmaceutical composition comprises glucose and fumarate. In some embodiments, the concentration of fumarate in the pharmaceutical compositions is between 0.1-10% (w/v). In some embodiments, the concentration of fumarate is between 0.1-5% (w/v). In some embodiments, the concentration of fumarate is between 0.1-1% (w/v). In some embodiments, the concentration of fumarate is between 0.1-0.5% (w/v). In some embodiments, the concentration of fumarate is about 0.4% (w/v). In some embodiments, the concentration of fumarate is about 0.2% (w/v).

In some embodiments, the pharmaceutical composition comprises between 0.1-10% (w/v) glucose and between 0.1-10% (w/v) fumarate. In some embodiments, the pharmaceutical composition comprises between 5-10% (w/v) glucose and between 5-10% (w/v) fumarate. In some embodiments, the pharmaceutical composition comprises between 0.1-5% (w/v) glucose and between 0.1-5% (w/v) fumarate. In some embodiments, the pharmaceutical composition comprises between 0.1-1% (w/v) glucose and between 0.1-1% (w/v) fumarate. In some embodiments, the pharmaceutical composition comprises between 0.1-0.5% (w/v) glucose and between 0.1-0.5% (w/v) fumarate. In some embodiments, the pharmaceutical composition comprises about 0.4% (w/v) glucose and about 0.4% (w/v) fumarate. In some embodiments, the pharmaceutical composition comprises about 0.2% (w/v) glucose and about 0.2% (w/v) fumarate.

In yet a further aspect, the pharmaceutical composition comprising a carbon source and an electron acceptor is formulated for administration to a human subject. In some embodiments, the pharmaceutical composition is formulated for parenteral administration. In some embodiments, the pharmaceutical composition is formulated for intravenous administration. In some embodiments, the pharmaceutical composition is formulated for enteral administration. In some embodiments, the pharmaceutical composition is formulated for oral administration. In some embodiments, the pharmaceutical composition is formulated for pulmonary administration. In some embodiments, the pharmaceutical composition is formalted for inhalation. For example, without wishing to be bound by any particular theory, the carbon source (e.g., glucose) can be nebulized in pure oxygen or in an $O_2$ enriched composition for pulmonary administration for pulmonary administration. In some embodiments, the pharmaceutical composition is formulated for local administration. In some embodiments, the pharmaceutical composition is formulated for topical administration. In some embodiments, the pharmaceutical composition formulated for topical administration is a cream, gel, lotion, or spray.

In another embodiment, the pharmaceutical composition comprises a quinolone antibiotic. In some embodiments, the quinolone antibiotic is a fluoroquinolone antibiotic. In some embodiments, the fluoroquinolone is ciprofloxacin, levofloxacin, or moxifloxacin. In some embodiments, the fluoroquinolone is ciprofloxacin. In some embodiments, the fluoroquinolone is levofloxacin. In some embodiments, the fluoroquinolone is moxifloxacin.

In yet a further aspect, the pharmaceutical composition comprising a quinolone antibiotic is formulated for administration to a human subject. In some embodiments, the pharmaceutical composition is formulated for parenteral administration. In some embodiments, the pharmaceutical composition is formulated for intravenous administration. In some embodiments, the pharmaceutical composition is formulated for enteral administration. In some embodiments, the pharmaceutical composition is formulated for oral administration. In some embodiments, the pharmaceutical composition is formulated for pulmonary administration. In some embodiments, the pharmaceutical composition is formalted for inhalation. For example, without wishing to be bound by any particular theory, the carbon source (e.g., glucose) can be nebulized in pure oxygen or in an $O_2$ enriched composition for pulmonary administration for pulmonary administration. In some embodiments, the pharmaceutical composition is formulated for local administration. In some embodiments, the pharmaceutical composition is formulated for topical administration. In some embodiments, the pharmaceutical composition formulated for topical administration is a cream, gel, lotion, or spray.

In some embodiments, the pharmaceutical composition comprises between 1 ng/mL and 10 μg/mL quinolone antibiotic. In some embodiments, the pharmaceutical composition comprises between 1 ng/mL and 1 μg/mL quinolone antibiotic. In some embodiments, the pharmaceutical compositions comprises between 1 ng/mL and 500 ng/mL quinolone antibiotic. In some embodiments, the pharmaceutical compositions comprises between 1500 ng/mL and 1 μg/mL quinolone antibiotic. In some embodiments, the pharmaceutical compositions comprises between 1 ng/mL and 100 ng/mL quinolone antibiotic. In some embodiments, the pharmaceutical compositions comprises between 100 ng/mL and 500 ng/mL quinolone antibiotic. In some embodiments, the pharmaceutical compositions comprises between 1 ng/mL and 50 ng/mL quinolone antibiotic. In some embodiments, the pharmaceutical compositions comprises between 50 ng/mL and 100 ng/mL quinolone antibiotic. In some embodiments, the pharmaceutical compositions comprises about 1 μg/mL quinolone antibiotic. In some embodiments, the pharmaceutical compositions comprises about 500 ng/mL quinolone antibiotic. In some embodiments, the pharmaceutical compositions comprises about 50 ng/mL quinolone antibiotic.

In some embodiments, the pharmaceutical composition comprises between 1 mg/mL and 50 mg/mL quinolone antibiotic. In some embodiments, the pharmaceutical compositions comprises between 20 mg/mL and 50 mg/mL quinolone antibiotic. In some embodiments, the pharmaceutical compositions comprises between 10 mg/mL and 20 mg/mL quinolone antibiotic. In some embodiments, the pharmaceutical composition comprises between 1 mg/mL and 10 mg/mL quinolone antibiotic. In some embodiments, the pharmaceutical compositions comprises between 5 mg/mL and 10 mg/mL quinolone antibiotic. In some embodiments, the pharmaceutical compositions comprises between 1 mg/mL and 5 mg/mL quinolone antibiotic. In some embodiments, the pharmaceutical compositions comprises between 1 mg/mL and 2 mg/mL quinolone antibiotic.

In some embodiments, the pharmaceutical composition comprises between 1 mg and 1000 mg quinolone antibiotic. In some embodiments, the pharmaceutical composition comprises between 750 mg and 1000 mg quinolone antibiotic. In some embodiments, the pharmaceutical composition comprises between 1 mg and 750 mg quinolone antibiotic. In some embodiments, the pharmaceutical composition comprises between 500 mg and 750 mg quinolone antibiotic. In some embodiments, the pharmaceutical composition comprises between 1 mg and 500 mg quinolone antibiotic.

In some embodiments, the pharmaceutical composition comprises between 250 mg and 500 mg quinolone antibiotic. In some embodiments, the pharmaceutical composition comprises between 1 mg and 250 mg quinolone antibiotic. In some embodiments, the pharmaceutical composition comprises between 250 mg and 100 mg quinolone antibiotic. In some embodiments, the pharmaceutical composition comprises between 1 mg and 100 mg quinolone antibiotic. In some embodiments, the pharmaceutical composition comprises between 50 mg and 100 mg quinolone antibiotic. In some embodiments, the pharmaceutical composition comprises between 1 mg and 50 mg quinolone antibiotic.

In yet a further aspect, the pharmaceutical composition comprises a carbon source, an electron acceptor, and a quinolone antibiotic. In some embodiments, the pharmaceutical composition comprises a fluoroquinolone antibiotic, glucose, and fumarate. In some embodiments, the pharmaceutical composition comprises a fluoroquinolone antibiotic and glucose, optionally wherein oxygen is present at or provided to an infection site. In some embodiments, the pharmaceutical composition comprises ciprofloxacin, glucose, and fumarate. In some embodiments, the pharmaceutical composition comprises levofloxacin, glucose, and fumarate. In some embodiments, the pharmaceutical composition comprises moxifloxacin, glucose, and fumarate. In some embodiments, the pharmaceutical composition further comprises one or more additional antibiotic agents.

In yet a further aspect, the pharmaceutical composition comprising a carbon source, an electron acceptor, and a quinolone antibiotic is formulated for administration to a human subject. In some embodiments, the pharmaceutical composition is formulated for parenteral administration. In some embodiments, the pharmaceutical composition is formulated for intravenous administration. In some embodiments, the pharmaceutical composition is formulated for enteral administration. In some embodiments, the pharmaceutical composition is formulated for oral administration. In some embodiments, the pharmaceutical composition is formulated for pulmonary administration. In some embodiments, the pharmaceutical composition is formalted for inhalation. For example, without wishing to be bound by any particular theory, the carbon source (e.g., glucose) can be nebulized in pure oxygen or in an $O_2$ enriched composition for pulmonary administration for pulmonary administration. In some embodiments, the pharmaceutical composition is formulated for local administration. In some embodiments, the pharmaceutical composition is formulated for topical administration. In some embodiments, the pharmaceutical composition formulated for topical administration is a cream, gel, lotion, or spray.

In certain embodiments, the carbon source, electron acceptor, and quinolone antibiotics described herein may be provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating an infection in a subject in need thereof. In certain embodiments, the effective amount is an amount effective for preventing the development of persister cells in a population of microorganisms. In certain embodiments, the effective amount is an amount effective for reducing the number of persister cells in a population of microorganisms. In certain embodiments, the number of persister cells is reduced by 2-fold, 5-fold, 10-fold, 15-fold, 20-fold, 50-fold, 100-fold, or 1000-fold upon administration of the pharmaceutical composition, compared to the number of persister cells present before administration of the pharmaceutical composition. In certain embodiments, the effective amount is an amount effective for eliminating the persister cells in a population of microorganisms. In some embodiments, the effective amount is an amount effective for eliminating (i.e., killing) the majority or all of the bacterial cells in a population of microorganisms. In some embodiments, the effective amount is an amount effective for eliminating (i.e., killing) the majority or all of the pathogenic bacterial cells in a population of microorganisms. In some embodiments, the effective amount is an amount effective for eliminating (i.e., killing) the majority or all of the infection-causing bacterial cells in a population of microorganisms. In some embodiments, the effective amount is an amount effective for curing the infection.

In yet a further embodiment, a pharmaceutical composition described herein may further comprise one or more additional antibiotic agents. The additional antibiotic agent may be useful in preventing or treating an infection in a subject in need thereof. For example, the additional antibiotic agent may be an antibiotic routinely administered for a bacterial infection, A person of ordinary skill in the art will be able to choose an appropriate additional antibiotic agent based on the microorganism(s) causing the infection to be treated in the subject. For example, multiple types of microorganisms may be present, such as, for example, a combination of *Staphylococcus aureus, Haemophilus influenzae*, and/or *Pseudomonas aeruginosa* as seen in lung infections in patients suffering from cystic fibrosis. In some embodiments, the additional antibiotic is an aminoglycoside, quinolone, macrolide, lincosamide, tetracycline, penicillin, cephalosporin, or polymyxin antibiotic. In some embodiments, the additional antibiotic agent is a second quinolone antibiotic. In some embodiments, the additional antibiotic agent is a second fluoroquinolone antibiotic.

Pharmaceutical compositions described herein can be prepared by any method known in the art of pharmacology. In general, such preparatory methods include bringing the composition described herein (i.e., the "active ingredient(s)") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient(s) (e.g., carbon source, electron acceptor, and/or quinolone antibiotic). The amount of the active ingredient is generally equal to the dosage of the active ingredient which would be administered to a subject and/or a convenient fraction of such a dosage, such as one-half or one-third of such a dosage. In some embodiments, a pharmaceutical composition comprising a carbon source and an electron acceptor is provided as a unit dose. In some embodiments, a pharmaceutical composition comprising a quinolone antibiotic is provided as a unit dose for use in combination with the pharmaceutical composition comprising a carbon source and an electron acceptor is provided as a unit dose. In some embodiments, a pharmaceutical composition comprising a carbon source, an electron acceptor, and a quinolone antibiotic is provided as a unit dose.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient(s) (e.g., carbon source, electron acceptor, quinolone antibiotic).

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition. Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug (e.g., a quinolone antibiotic), it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient(s) (e.g., carbon source, electron acceptor, and/or quinolone antibiotic) and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient(s), and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

In some embodiments, one or more agents in the pharmaceutical composition is encapsulated in a nanoparticle, micelle, or liposome for delivery and/or administration. The term "nanoparticle" refers to a particle having an average (e.g., mean) dimension (e.g., diameter) of between about 1 nanometer (nm) and about 1 micrometer (μm) (e.g., between about 1 nm and about 300 nm, between about 1 nm and about 100 nm, between about 1 nm and about 30 nm, between about 1 nm and about 10 nm, or between about 1 nm and about 3 nm), inclusive.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. Quinolones specifically utilized in veterinary pharmacology, as opposed to the treatment of human subjects, are well known in the art.

Compositions provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The pharmaceutical compositions provided herein can be administered by any route, including enteral (e.g., oral), parenteral, intravenous, intramuscular, intra-arterial, rectal, intravaginal, mucosal, nasal, bucal, sublingual, topical; by intratracheal instillation, bronchial instillation, and/or inhalation; and/or as an oral spray, nasal spray, and/or aerosol. Specifically contemplated routes are oral administration, intravenous administration (e.g., systemic intravenous injection), pulmonary administration, and/or local (i.e., direct) administration to an affected site. "Local administration" generally refers to a route of administration that deliers the pharmaceutical composition directly to the site of action (e.g., topical administration via creams, lotions, sprays, and the like). In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the subject.

The exact amount of a composition or multiple compositions (e.g., two different compositions) required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses, an oral dose in combination with an intravenous dose, and the like). In certain embodiments, when multiple doses are administered to a subject, any two doses of the multiple doses include different or substantially the same amounts of a compound described herein. In certain embodiments, when multiple doses are administered to a subject, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject is one dose per day. In certain embodiments, the frequency of administering the multiple doses to the subject is two doses per day. In certain embodiments, the frequency of administering the multiple doses to the subject is three doses per day. In certain embodiments, when multiple doses are administered to a subject, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject. In certain embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a composition described herein. In certain embodiments, a dose described herein includes independently between 1 mg and 1,000 mg, inclusive, of a composition described herein. In certain embodiments, a dose described herein includes independently between 1 mg and 750 mg, inclusive, of a composition described herein. In certain embodiments, a dose described herein includes independently between 1 mg and 500 mg, inclusive, of a composition described herein. In certain embodiments, a dose described herein includes independently between 1 mg and 250 mg, inclusive, of a composition described herein. In certain embodiments, a dose described herein includes independently between 1 mg and 100 mg, inclusive, of a composition described herein. In certain embodiments, a dose described herein includes independently between 1 mg and 50 mg, inclusive, of a composition described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating an infection in a subject in need thereof, in preventing an infection in a subject in need thereof, in reducing the risk to develop an infection in a subject in need thereof, improve bioavailability, improve safety, reduce drug resistance, reduce and/or modify metabolism, inhibit excretion, and/or modify distribution in a subject or cell. It will also be appreciated that the therapy employed may achieve a desired effect for the same infection, and/or it may achieve different effects. In certain embodiments, a pharmaceutical composition described herein and an additional pharmaceutical agent shows a synergistic effect that is absent in a pharmaceutical composition including one of the compound and the additional pharmaceutical agent, but not both. In some embodiments, the additional pharmaceutical agent is an anti-inflammatory agent, immunosuppressant, anti-bacterial agent, or anti-viral agent. In some embodiments, the additional pharmaceutical agent is an antibiotic agent. In some embodiments, the antibiotic agent is a quinolone. In some embodiments, the antibiotic agent is a fluoroquinolone.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing an infection. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

Also encompassed by the disclosure are kits (e.g., pharmaceutical packs). The kits provided may comprise a pharmaceutical composition described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form. In some embodiments, a pharmaceutical composition comprising a carbon source and an electron acceptor is provided in the first container and a pharmaceutical composition comprising a quinolone antibiotic is provided in the second container. In certain embodiments, a kit described herein further includes instructions for using the kit.

A kit described herein may also include information as required by a regulatory agency such as the U.S. Food and Drug Administration (FDA). In certain embodiments, the information included in the kits is prescribing information. In certain embodiments, the kits and instructions provide for treating an infection in a subject in need thereof. In certain embodiments, the kits and instructions provide for preventing an infection in a subject in need thereof. In certain embodiments, the kits and instructions provide for reducing the risk of developing an infection in a subject in need thereof. A kit described herein may include one or more additional pharmaceutical agents described herein as a separate composition.

Methods of Use

As described above, in some aspects, the disclosure provided herein is based on a mechanism for priming respiratory metabolism by the addition of a carbon source and electron acceptor to affect both target corruption and other less-characterized, downstream processes, thereby sensitizing persistent cells to quinolone antibiotics. For example, as shown in Examples 2 and 3, a combination of a carbon source and an electron acceptor sensitizes a population comprising one or more persistent cells to a quinolone antibiotic. It is important to note that quinolone killing is enhanced only when both the carbon source and the electron acceptor are present, i.e., they have a synergistic effect on sensitization (See, e.g., FIG. 2E and FIG. 3A).

Thus, in one aspect, described herein is a method for sensitizing a microorganism to an antibiotic. In some embodiments, the microorganisms are sensitized to a quinolone antibiotic. In some embodiments, the method comprises (i) contacting the microorganism with an effective amount of a carbon source, and (ii) contacting the microorganism with an effective amount of an electron acceptor. In some embodiments, step (i) is performed before step (ii) (i.e., sequentially). In some embodiments, step (ii) is performed before step (i) (i.e., sequentially). In some embodiments, step (i) and step (ii) are performed simultaneously. In some embodiments, the microorganism is present in a population of one or more microorganisms, wherein the population of microorganisms comprises one type or multiple different types of microorganisms. In some embodiments, the population of microorganisms is a high-density population. In some embodiments, the microorganism is a bacterium. In some embodiments, the bacterium is a gram positive bacterium. In some embodiments, the gram positive bacterium is a member of the genus *Staphylococcus* or *Streptococcus*. In some embodiments, the bacterium is *Staphylococcus aureus*. In some embodiments, the bacterium is *Mycobacterium smegmatis*. In some embodiments, the bacterium is a gram negative bacterium. In some embodiments, the bacterium is *Escherichia coli*. In some embodiments, the bacterium is *Pseudomonas aeruginosa*. In some embodiments, the bacterium is *Haemophilus influenzae*. In some embodiments, the quinolone antibiotic is a fluoroquinolone antibiotic. In some embodiments, the fluoroquinolone antibiotic is ciprofloxacin. In some embodiments, the fluoroquinolone antibiotic is levofloxacin. In some embodiments, the fluoroquinolone antibiotic is moxifloxacin. In some embodiments, the carbon source is an intermediate in glycolysis. In some embodiments, the carbon source is a furanose sugar. In some embodiments, the carbon source is a pyranose sugar. In some embodiments, the carbon source is glucose. In some embodiments, the electron acceptor is fumarate. In some embodiments, the electron acceptor is oxygen. In some embodiments, the oxygen is present at an infection site, wherein the infection site is comprised of a population of microorganisms. In some embodiments, the oxygen is provided to an infection site, wherein the infection site is comprised of a population of microorganisms. In some embodiments, the population of microorganisms comprises one or more antibiotic persistent microorganism. In some embodiments, the antibiotic persistent microorganism is a type I persister. In some embodiments, the microorganism is in vitro. In some embodiments, the microorganism is in vivo. In some embodiments, the microorganism is in an organism.

In another aspect, described herein is a method is a method for preventing or reducing the density-dependent persistence (DDP) of a microorganism. In some embodiments, the method comprises contacting a population of microorganisms comprised of one or more antibiotic persistent cells with (i) an effective amount of a carbon source, and (ii) an effective amount of an electron acceptor. In some embodiments, the population of microorganisms is in vitro. In some embodiments, the population of microorganisms is in vivo. In some embodiments, the method further comprises contacting the population of microorganisms with an effective amount of a quinolone antibiotic. In some embodiments, the quinolone antibiotic is a fluoroquinolone antibiotic. In some embodiments, the fluoroquinolone antibiotic is ciprofloxacin. In some embodiments, the fluoroquinolone antibiotic is levofloxacin. In some embodiments, the fluoroquinolone antibiotic is moxifloxacin. In some embodiments, the population of microorganisms is contacted with a first pharmaceutical composition comprising the carbon source and the election acceptor, and a second pharmaceutical composition comprising the quinolone antibiotic. In some embodiments, the method further comprises contacting the population of microorganisms with an effective amount of a second antibiotic agent. In some embodiments, the antibiotic persistent cell is a bacterium. In some embodiments, the bacterium is a gram positive bacterium. In some embodiments, the gram positive bacterium is a member of the genus *Staphylococcus* or *Streptococcus*. In some embodiments, the bacterium is *Staphylococcus aureus*. In some embodiments, the bacterium is *Mycobacterium smegmatis*. In some embodiments, the bacterium is a gram negative bacterium. In some embodiments, the bacterium is *Escherichia coli*. In some embodiments, the bacterium is *Pseudomonas aeruginosa*. In some embodiments, the bacterium is *Haemophilus influenzae*. In some embodiments, the carbon source is an intermediate in glycolysis. In some embodiments, the carbon source is a furanose sugar. In some embodiments, the carbon source is a pyranose sugar. In some embodiments, the carbon source is glucose. In some embodiments, the electron acceptor is fumarate. In some embodiments, the electron acceptor is oxygen. In some embodiments, the oxygen is present at an infection site, wherein the infection site is comprised of a population of microorganisms. In some embodiments, the oxygen is provided to an infection site, wherein the infection site is comprised of a population of microorganisms. In some embodiments, the population of microorganisms is a high-density population.

In yet another aspect, described herein is a method for preventing, reducing, or eliminating persister cells in a population of microorganisms. In some embodiments, the method comprises (i) contacting the cells with an effective amount of a carbon source, (ii) contacting the cells with an effective amount of an electron acceptor, and (iii) contacting the cells with an effective amount of a quinolone antibiotic. In some embodiments, the population of microorganisms is contacted with a first pharmaceutical composition comprising the carbon source and the election acceptor, and a second pharmaceutical composition comprising the quinolone antibiotic. In some embodiments, the quinolone antibiotic is a fluoroquinolone antibiotic. In some embodiments, the fluoroquinolone antibiotic is ciprofloxacin. In some embodiments, the fluoroquinolone antibiotic is levofloxacin. In some embodiments, the fluoroquinolone antibiotic is moxifloxacin. In some embodiments, step (iii) comprises contacting the cells with a combination of a quinolone antibiotic and one or more additional antibiotic agents. In some embodiments, the persister cell is a bacterium. In some embodiments, the bacterium is a gram positive bacterium. In some embodiments, the gram positive bacterium is a member of the genus *Staphylococcus* or *Streptococcus*. In some embodiments, the bacterium is *Staphylococcus aureus*. In some embodiments, the bacterium is *Mycobacterium smegmatis*. In some embodiments, the bacterium is a gram negative bacterium. In some embodiments, the bacterium is *Escherichia coli*. In some embodiments, the bacterium is *Pseudomonas aeruginosa*. In some embodiments, the bacterium is *Haemophilus influenzae*. In some embodiments, the carbon source is an intermediate in glycolysis. In some embodiments, the carbon source is a furanose sugar. In some embodiments, the carbon source is a pyranose sugar. In some embodiments, the carbon source is glucose. In some embodiments, the electron acceptor is fumarate. In some embodiments, the electron acceptor is oxygen. In some embodiments, the oxygen is present at an infection site, wherein the infection site is comprised of a population of microorganisms. In some embodiments, the oxygen is provided to an infection site, wherein the infection site is comprised of a population of microorganisms. In some embodiments, the population of microorganisms is a high-density population.

In yet another aspect, described herein is a method for preventing or treating an infection in a subject in need thereof, wherein the infection is comprised of a population of microorganisms comprising one or more persister cells. In some embodiments, the method comprises (i) administering to the subject an effective amount of a carbon source, (ii) administering to the subject an effective amount of an electron acceptor, and (iii) administering to the subject an effective amount of a quinolone antibiotic. In some embodiments, a first pharmaceutical composition comprising the carbon source and the election acceptor is administered to the subject, and a second pharmaceutical composition comprising the quinolone antibiotic is administered to the subject. In some embodiments, the first pharmaceutical composition is formulated for pulmonary, topical, enteral, or parenteral administration. In some embodiments, the second pharmaceutical composition is formulated for parenteral or enteral administration. In some embodiments, the second pharmaceutical composition is formulated for intravenous administration. In some embodiments, the quinolone antibiotic is a fluoroquinolone antibiotic. In some embodiments, the fluoroquinolone antibiotic is ciprofloxacin. In some embodiments, the fluoroquinolone antibiotic is levofloxacin. In some embodiments, the fluoroquinolone antibiotic is moxifloxacin. In some embodiments, the carbon source is an intermediate in glycolysis. In some embodiments, the carbon source is a furanose sugar. In some embodiments, the carbon source is a pyranose sugar. In some embodiments, the carbon source is glucose. In some embodiments, the electron acceptor is fumarate. In some embodiments, the electron acceptor is oxygen. In some embodiments, the oxygen is present at an infection site, wherein the infection site is comprised of a population of microorganisms. In some embodiments, the oxygen is administered directly to an infection site, wherein the infection site is comprised of a population of microorganisms. In some embodiments, the population of microorganisms is a high-density population. In some embodiments, the population of microorganisms comprises one or more persister cells. In some embodiments, the persister cell is a bacterium. In some embodiments, the bacterium is a gram positive bacterium. In some embodiments, the gram positive bacterium is a member of the genus *Staphylococcus* or *Streptococcus*. In some embodiments, the bacterium is *Staphylococcus aureus*. In some embodiments, the bacterium is *Mycobacterium smegmatis*. In some embodiments, the bacterium is a gram negative bacterium. In some embodiments, the bacterium is *Escherichia coli*. In some embodiments, the bacterium is *Pseudomonas aeruginosa*. In some embodiments, the bacterium is *Haemophilus influenzae*.

EXAMPLES

Example 1. Quinolone Activity Against *E. Coli* is Dependent on Growth Phase

Figure 1B:
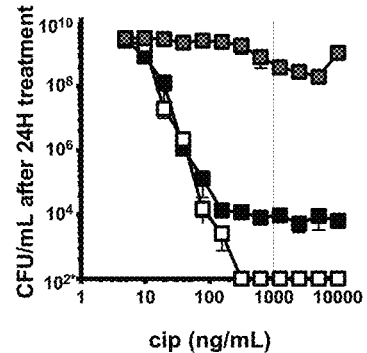
Figure 1C:
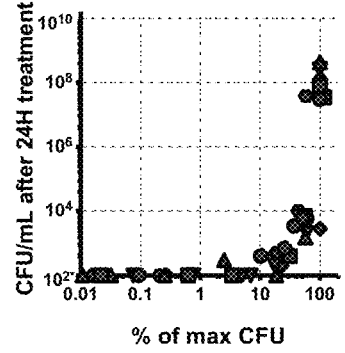
Figure 7A:
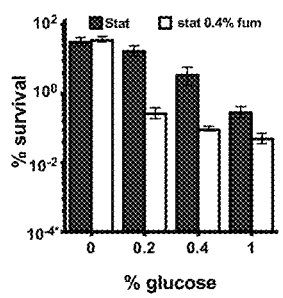
FIGS. 7A-7F. Glucose-fumarate potentiation.
Figure 7B:
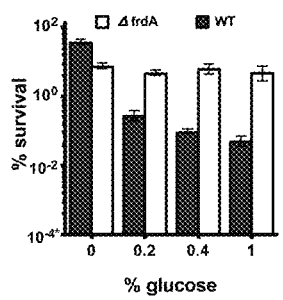
Figure 7C:
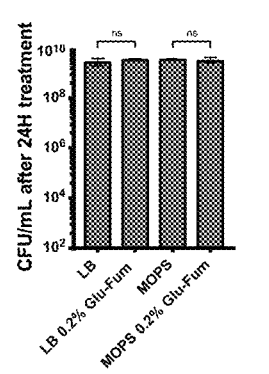
Figure 7D:
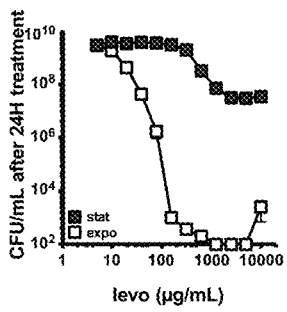
Figure 7E:
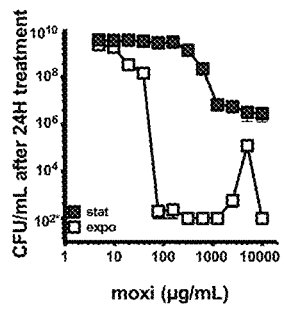

Ciprofloxacin is a widely used second-generation quinolone. With a minimum inhibitory concentration (MIC) of 8-10 ng/mL in rich LB medium targeting *E. coli* strain MG1655, it is one of the most potent drugs of the quinolone family. However, the lethal effect of ciprofloxacin decreases as the bacterial population grows to higher cell density (FIG. 1A-C). Alternative fluoroquinolones from the third generation (levofloxacin) and fourth generation (moxifloxacin) show similar density-dependent effects (FIGS. 7D and 7E). Quinolone potency is highest during exponential growth at low cell density (<1% of maximal growth), and starts to reduce as soon as cells reach 10% of the maximal carrying capacity in LB media (around $10^8$ cells). This DDP is characterized by the inability of ciprofloxacin to kill a fraction of the cell population, even with a dose representing 1000× the MIC and a treatment time of 24 hours (FIG. 1B). The fraction of surviving cells significantly increases upon entry into stationary phase (FIG. 1A-C) and represents 10 to 100% of the population depending on the drug concentration used for the treatment.

Figure 5A:
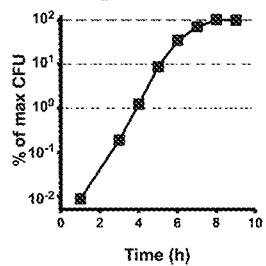
FIGS. 5A-5I. *E. coli* density-dependent persistence to ciprofloxacin.
Figure 5B:
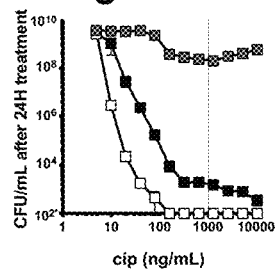
Figure 5C:
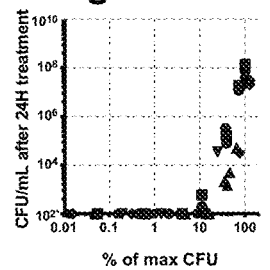
Figure 5D:
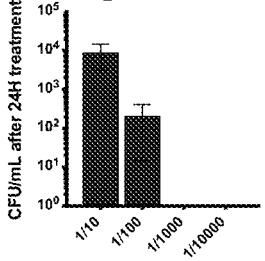
Figure 5E:
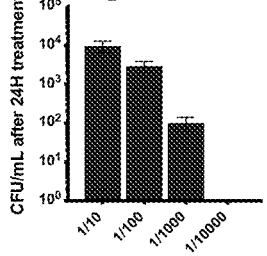

In order to study DDP to ciprofloxacin in more detail, we tested a range of cultivation conditions. We treated cells with 1 μg/mL ciprofloxacin (100×MIC) as this concentration achieved maximal killing at low cell density and retained cell killing at intermediate cell density (FIG. 1B). We further conducted our experiments in MOPS rich media to ensure that the DDP observed in LB is conserved across discrete growth conditions (FIG. 5A-C). Consistent with previous reports, we found that an initial dilution of 1/10,000 from overnight cultures was necessary to avoid pre-existing cells being able to persist to our concentration range (FIGS. 5D and 5E) (Brauner et al., 2016).

Figure 5F:
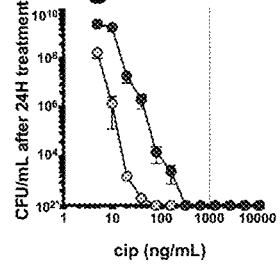
Figure 5G:
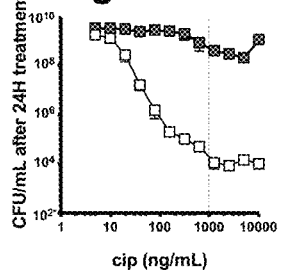
Figure 5H:
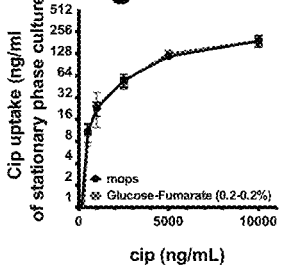

To exclude the possibility that DDP to ciprofloxacin was entirely a consequence of impaired drug uptake, we examined density-dependent susceptibility of a quinolone hypersensitive mutant recB, which is unable to repair DNA double-stranded breaks. This mutant is still hypersensitive in stationary phase (FIGS. 5F and 5G), suggesting that DDP to ciprofloxacin is not exclusively due to reduced diffusion of the drug. We confirmed these data by performing uptake measurements of ciprofloxacin by stationary phase cells (FIG. 5H). We found that within 30 min, stationary phase bacteria were able to accumulate ciprofloxacin in a dose-dependent manner. From this finding, we hypothesized that stationary phase cells may still be damaged by quinolones, however the damage leads to limited cell death in wildtype cells under these conditions. We thus hypothesized that environmental constraints could be an additional factor in quinolone DDP.

Figure 1D:
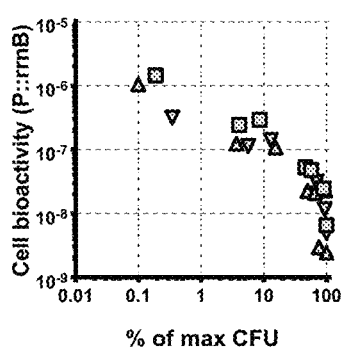

To test this hypothesis, we examined the expression of an unstable GFP variant under the control of the ribosomal RNA promoter P1 (P1rrnB) (Maisonneuve et al., 2013; Mathieu et al., 2016), the activity of which has been shown to correlate with the overall ability of the cells to grow as well as the formation of persister cells. We observed a gradual decrease in GFP expression as the cell population increased, followed by a steep drop in fluorescence corresponding to entry into stationary phase (FIG. 1D). This drop-off in P1rrnB activity correlated with the large increase in ciprofloxacin persistence observed in high-density cultures (FIG. 1C). P1rrnB activity can be modulated by starvation signaling through the stringent response or alternatively by the depletion of cellular energy stores from nucleic acid triphosphate molecules (ATP, GTP) (Paul et al., 2004).

Figure 1E:
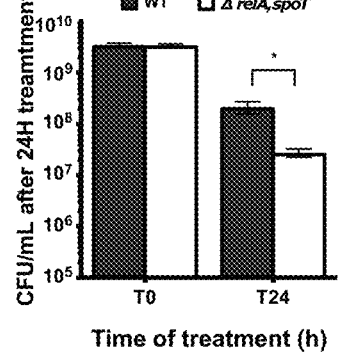
Figure 1F:
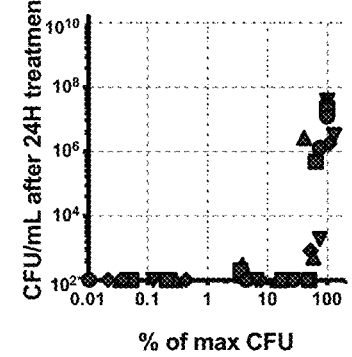
Figure 5I:
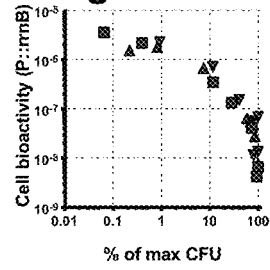

As this ribosomal promoter element has been used as a proxy for persister cells, (Maisonneuve et al., 2013), we applied this system to explore the contribution of the guanosine tetraphosphate (ppGpp)-mediated stringent response on DDP to ciprofloxacin. Persistence of *E. coli* to bactericidal antibiotics, including ciprofloxacin, has been linked with the stringent response, which is modulated by production of high levels of ppGpp by the enzymes RelA and SpoT. We investigated the contribution of the *E. coli* stringent response to DDP to ciprofloxacin using ppGpp$^0$ strain, ΔrelAspoT. Consistent with previous data (Maisonneuve et al., 2013), we found that a stationary phase ΔrelAspoT mutant displayed a 5.5-fold reduction in persister cells compared to wildtype (FIG. 1E). We next assessed the accumulation of persister cells over varying cell densities in the ΔrelAspoT background. Though the total number of persister cells is reduced relative to wildtype, the ΔrelAspoT mutant retains a marked DDP phenotype (FIG. 1F). We measured the activity of the P1rrnB promoter in the ΔrelAspoT background, and the effective drop in expression occurring in stationary phase was independent of the production of ppGpp (FIG. 5I). These findings suggest that starvation itself, rather than the induction of the stringent response, is critical for DDP to ciprofloxacin.

Figure 2A:
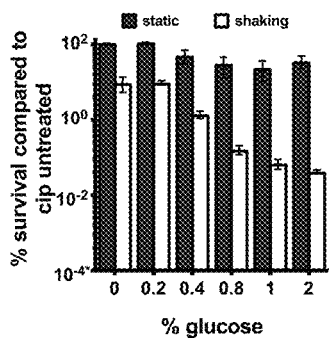
FIGS. 2A-2F. *E. coli* dissolved oxygen concentration limits ciprofloxacin sensitivity at high cell density.

Example 2. Both Carbon and Oxygen are Necessary to Sensitize Stationary Phase Cells to Quinolone Antibiotic We next sought to elucidate the factors limiting cell death at high cell density. To have greater control on the metabolic inputs in the culture, we used defined MOPS rich media for these experiments. We first assessed if stationary phase carbon depletion was responsible for DDP to ciprofloxacin. Consistent with earlier reports (Allison et al., 2011), addition of glucose to stationary phase cultures promoted minimal increases of ciprofloxacin activity. Sensitization to 1 μg/mL of ciprofloxacin by glucose was dose-dependent starting at 0.4% with a plateau at 1% glucose (FIG. 2A).

Figure 2B:
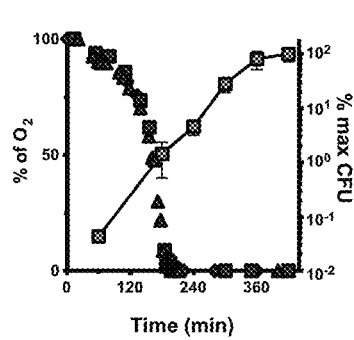
Figure 2C:
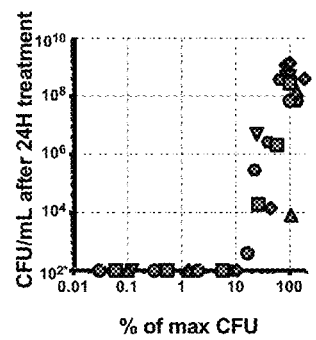
Figure 2D:
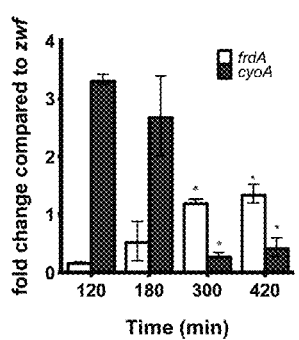

Because oxygen is a known limiting growth factor at high cell density (Losen et al., 2004) and a known variable limiting quinolone sensitivity (Lewin et al., 1991), we next evaluated the effect of media oxygenation on ciprofloxacin activity in the presence and absence of supplementary glucose. To this end, we measured and modulated steady-state oxygen concentrations in static culture systems (FIGS. 2A and 2B). Using this approach, we first examined stationary phase cell sensitivity to ciprofloxacin in static culture (FIG. 2A). Notably, static cultures displayed the identical DDP to ciprofloxacin (FIG. 2C). Importantly, we observed that static cultures receiving no aeration showed no sensitization to glucose supplementation (FIGS. 2A and 2D). This observation suggested the possibility that glucose supplementation can partially restore the activity of quinolone antibiotics only under aerated growth conditions.

To further explore aeration-dependent ciprofloxacin activity, we measured dissolved oxygen as a function of growth density using a solid-state oxygen detector sensitive to molecular oxygen at 8 ppb under static growth conditions (FIG. 2B). We found that dissolved oxygen dropped below the detection limit at 220 min of growth, corresponding to a population density of $5^{e7}$ cells, or 5% of maximal growth. Continuous monitoring of stationary phase cultures in static growth conditions showed that dissolved oxygen levels remained below our detection limit even after 24 hours of static incubation (FIG. 2B).

To confirm that bacterial cells were responding physiologically to changes in oxygen tension as culture density increased consistent with an aerobic-to-anaerobic transition, we measured gene expression of two genes known to be differentially regulated by the oxygen concentration. Using qPCR, we compared the expression of the main cytochrome oxidase (cyoA) and the anaerobic fumarate reductase gene (frdA) to the expression of the housekeeping gene zwf (Tseng et al., 1996) (FIG. 2D). We found expression patterns typical of an aerobic-to-anaerobic shift, demonstrating progressive cyoA down-regulation and increasing frdA expression as the population density increased. Thus in static culture (FIG. 2D), as cell density increases, the bacterial population adapts physiologically by reorganizing its electron transport chain in a manner consistent with reduced oxygen availability, further suggesting that oxygen starvation is present in high-density cultures.

Figure 2E:
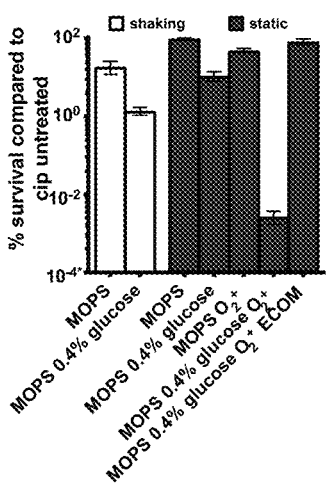
Figure 6A:
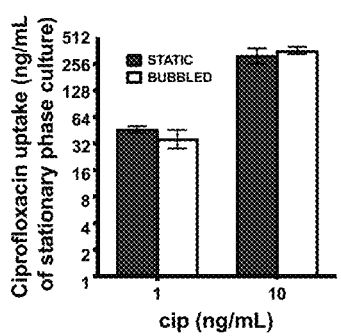
FIGS. 6A-6C. *E. coli* electron transport chain is essential to the sensitization by oxygen and glucose.
Figure 6B:
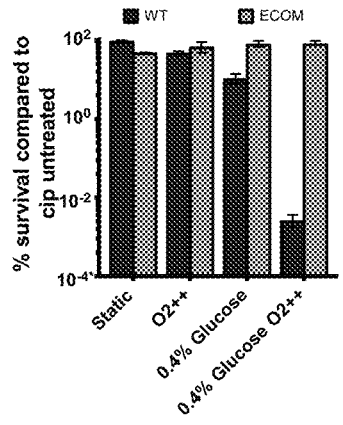
Figure 6C:
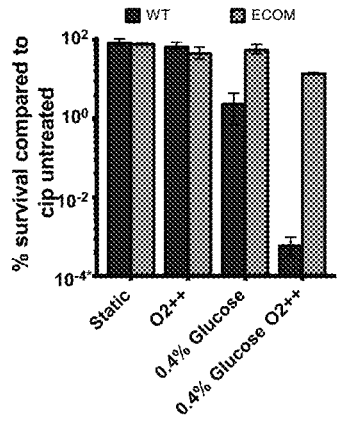

To test the hypothesis that both carbon and oxygen constitute simultaneous limiting factors in DDP to ciprofloxacin, we evaluated antibiotic susceptibility of static cultures receiving defined oxygen supplementation. We provided oxygen by bubbling filtered air into the media at a calibrated rate (10 psi) to maintain a steady-state oxygen tension of 5-6% in the static stationary phase cultures. Consistent with our hypothesis, we found that stationary phase E. coli was highly susceptible to ciprofloxacin when exposed to a combination of glucose and oxygen, while addition of glucose or oxygen alone had minimal effect (FIG. 2E). Under this specific level of glucose supplementation (0.4%), the degree of killing under static conditions with oxygen supplementation exceeded killing found in the optimized shaking condition (FIGS. 2A and 2E). We next assessed the influence of this treatment on ciprofloxacin uptake, and found no difference between control and metabolite-supplemented cultures (FIG. 6A). Taken together, these data suggest that DDP to ciprofloxacin in static growth conditions is mediated by blocks to cellular respiration imposed by limitations in both carbon and oxygen, and that supply of these two factors is sufficient to sensitize high-density cultures to ciprofloxacin. To further assess this hypothesis, we attempted to sensitize a well characterized E. coli strain (ECOM) that is limited to fermentative metabolism under aerobic conditions due to deletion of the complete cytochrome oxidase loci and a quinol monoxygenase (Portnoy et al., 2008). This strain is genetically incapable of coupling molecular oxygen to oxidative phosphorylation. Consistent with our hypothesis, the ECOM strain was insensitive to ciprofloxacin at high density when provided supplemental glucose and oxygen (FIG. 2E and FIG. 6B-6C).

Figure 2F:
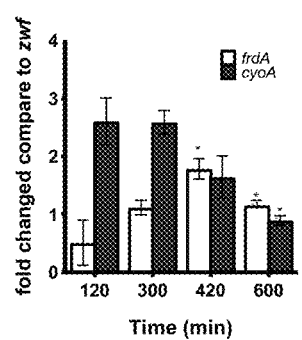

Since we observed increased killing in the oxygen-supplemented static cultures relative to shaking cultures (FIGS. 2A and 2E), we hypothesized that aeration may be limited even under optimized shaking conditions, and thus that oxygen may be a limiting factor in this setting. Due to the physical constraints of the system, we were not able to confidently measure dissolved-oxygen in our shaking conditions with the oxygen probe. As a proxy for aero-anaerobic transition, we evaluated the expression levels of cyoA and frdA in shaking cultures, and found that cyoA and frdA expression pattern were similar in both shaking and static cultures further suggesting that oxygen tension is limiting even when cultures are optimally aerated by shaking (FIG. 2F).

Figure 3A:
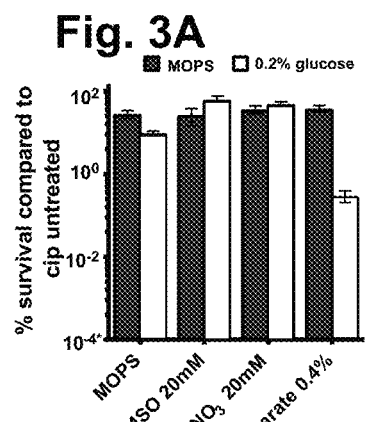
FIGS. 3A-3F. Fumarate respiration-dependent sensitization to ciprofloxacin by glucose.
Figure 7F:
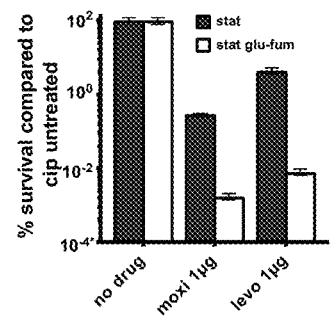

Example 3. Fumarate can Substitute Oxygen as an Electron Acceptor to Sensitize Bacteria to Quinolone Antibiotics The E. coli respiration system is highly versatile and the quinol pool can transfer electrons to substrates other than oxygen. We asked if anaerobic respiration could also lead to glucose-dependent sensitization to ciprofloxacin in stationary phase. We tested nitrate, DMSO, and fumarate as alternative electron acceptors in MOPS rich media under shaking conditions (FIG. 3A). While none of these electron acceptors alone was able to sensitize cells to ciprofloxacin, we found that in combination with glucose, fumarate synergistically sensitized high-density cultures to 1 µg/mL ciprofloxacin in a manner similar to oxygen supplementation (FIG. 3A and FIG. 7A-7B). Similar synergy was observed using the third- and fourth-generation quinolone antibiotics, levofloxacin and moxifloxacin, respectively (FIG. 7F), indicating conservation of the phenotype across the chemical generations of quinolones. Increasing glucose above 0.2% did not enhance killing in conjunction with fumarate (FIG. 7A), indicating again that carbon source availability is required, but not strictly limiting, for DDP to ciprofloxacin.

Figure 3B:
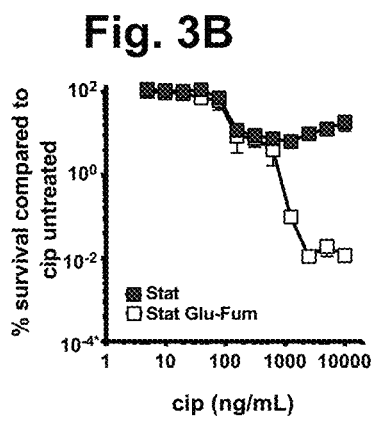
Figure 3C:
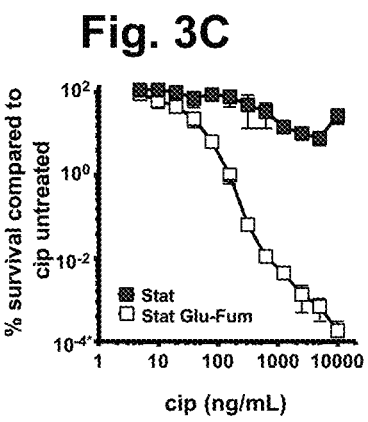

We next assessed the dose-dependent relationship of ciprofloxacin sensitization to the combination of glucose and fumarate. While sensitization was limited to concentrations above 500 ng/mL of ciprofloxacin for the MOPS rich media (FIG. 3B), stationary phase cells grown in LB supplemented with glucose and fumarate were killed by ciprofloxacin at concentrations as low as 50 ng/mL (FIG. 3C).

Figure 3D:
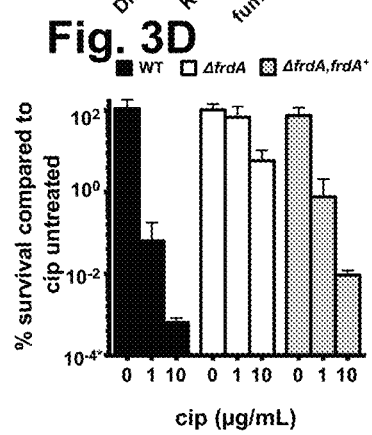

As our data suggested that cellular respiration was a limiting factor for sensitization by glucose, we wanted to confirm that in our condition cells used fumarate as a terminal electron acceptor. We thus tested ciprofloxacin sensitivity at high cell density of a mutant strain lacking the catalytic subunit of the fumarate reductase gene, frdA. We found that the frdA mutant was not able to be sensitized to ciprofloxacin killing by the combination glucose-fumarate, suggesting a direct role of alternative respiration through fumarate reduction as a key factor in sensitizing cells to ciprofloxacin (FIG. 3D and FIG. 7B). Complementation of the frdA mutant using a plasmid expressing the frdA gene under the control of the native promoter restored sensitization to ciprofloxacin by glucose and fumarate supplementation (FIG. 3D).

We next sought to better understand how the enzymatic reduction of fumarate leads to cell death by ciprofloxacin.

Figure 3E:
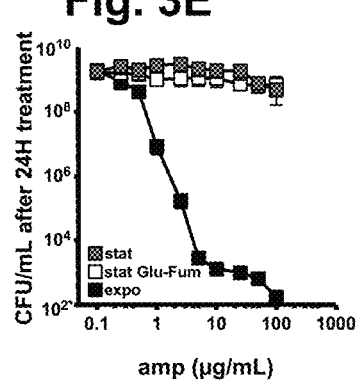
Figure 3F:
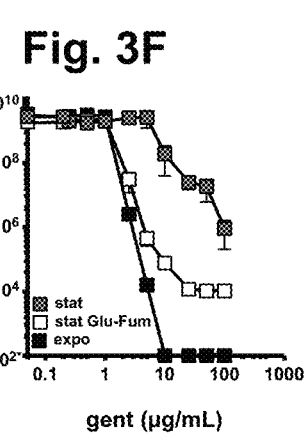

We hypothesized that the addition of fumarate was sensitizing cells by specifically increasing cellular respiration (FIG. 2E) as a component of overall cellular metabolism rather than simply driving cell division. Although we did not observe a significant increase in CFU over time after the addition of glucose and fumarate (FIG. 7C), we decided to use a more sensitive method to differentiate cellular respiration and cell growth. To assess this, we asked whether glucose-fumarate supplementation could sensitize stationary phase cells to ampicillin (FIG. 3E), a β-lactam antibiotic that requires cell division for killing, or gentamicin (FIG. 3F), which requires an active metabolism and the generation of a proton motive force for drug uptake. Confirming our original hypothesis, glucose-fumarate supplementation sensitized stationary phase *E. coli* to gentamicin; however, even high concentrations of ampicillin did not kill stationary phase cells with glucose-fumarate supplementation, further supporting the hypothesis that metabolite addition was not inducing significant cell growth in high-density cultures.

Example 4. Carbon Source and Electron Acceptor Availability Limits Quinolone Antibiotic Activity in *S. Aureus* and *M. Smegmatis*

Figure 4A:
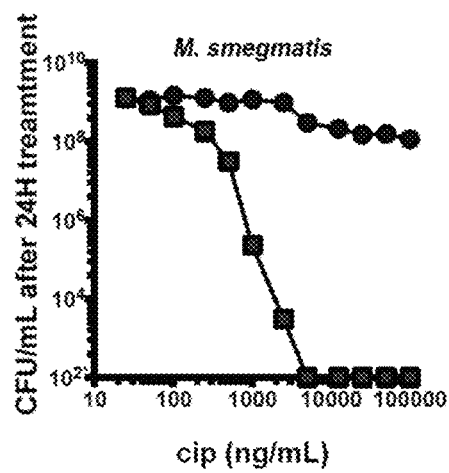
FIGS. 4A-4D. Sensitization to ciprofloxacin in clinically relevant pathogens.
Figure 4B:
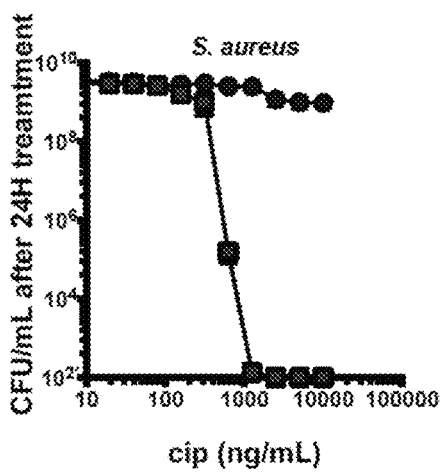

Having defined a mechanistic context for DDP to ciprofloxacin in a Gram-negative enterobacterium, we next tested whether our findings were generalizable to two additional bacteria, *S. aureus* (MIC: 250 μg/ml) and *M. smegmatis* (MIC: 500 ng/ml). Though ciprofloxacin alone was not as potent for treating *S. aureus* and *M. smegmatis* in exponentially growing cultures as for *E. coli*, higher doses could successfully reduce the number of viable cells below the limit of detection for both species (FIGS. 4A and 4B). Similar to *E. coli*, *S. aureus* and *M. smegmatis* exhibit marked DDP to ciprofloxacin upon entry into stationary phase (FIGS. 4A and 4B).

Figure 4C:
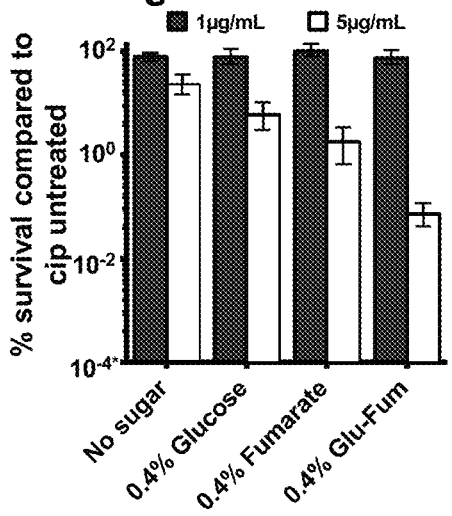
Figure 4D:
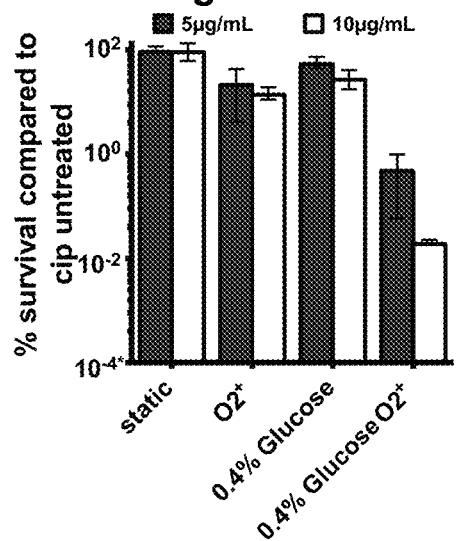

Because the *M. smegmatis* genome includes several putative fumarate reductase enzymes (Caspi et al., 2016), we attempted to sensitize aerated stationary phase cultures to ciprofloxacin by using a combination of glucose and fumarate (FIG. 4C). We found that while 0.4% fumarate or 0.4% glucose alone could sensitize cultures weakly, the combination of both compounds strongly sensitized *M. smegmatis* stationary phase cultures. *S. aureus* is not able to use fumarate as an alternative electron acceptor (Fuchs et al., 2007). Thus, we tried sensitizing *S. aureus* stationary cultures to ciprofloxacin by the combination of oxygen and glucose (FIG. 4D). While the addition of glucose or bubbling had a limited effect on ciprofloxacin activity, the addition of 0.4% glucose together with bubbling sensitized *S. aureus* static cultures to 5 and 10 μg/mL of ciprofloxacin. These observations indicate that the stimulation of metabolism specifically at the level of cellular respiration is a broadly applicable method to sensitize a range of bacteria to ciprofloxacin.

Discussion

DDP to quinolone antibiotics is a known phenotype without a defined mechanism (Zeiler, 1985). Here we show that external limits to specific metabolic pathways, rather than the cellular response to starvation, are the key factors modulating quinolone activity under high cell-density conditions. While carbon sources are limiting, replenishment of carbon oxidation pathways alone is insufficient for ciprofloxacin activity, and the availability of a suitable terminal electron acceptor is critical to regenerate lethal activity of quinolone antibiotics in high cell-density settings. With this framework, we propose a simple, two-input metabolite-driven strategy to stimulate the activity of ciprofloxacin against a range of bacteria at high densities. The implications for therapeutic implementation of this strategy warrant further studies.

An emerging model for bacterial persistence to antibiotics has focused on physiologic adaptation to starvation, as mediated by the stringent response (Harms et al., 2016). A key finding from our work, in particular using a ppGpp$^0$ strain, is that starvation itself rather than cellular adaptations to starvation is the major driving force in DDP. Antibiotic persistence has been described to derive from two physiologic processes that are either induced or stochastic, referred to as Type I and Type II persisters (Levin-Reisman and Balaban, 2016). In our work, it is important to note that we have focused on induced, type I persisters specifically and that conclusions drawn here cannot necessarily be applied to stochastically formed persisters, which exist in our sensitized cultures after treatment.

While *E. coli* can oxidize carbon and generate ATP through fermentation, we find that cell killing by ciprofloxacin requires activity of respiratory metabolic pathways, which can be accomplished by a limited number of metabolic inputs. It is known that topoisomerase activity is ATP-dependent, and that stationary phase cells require topoisomerases to recover supercoiling (Gutierrez-Estrada et al., 2014), suggesting that starvation states may limit the activity of these enzymes. Furthermore, increased cellular respiration is implicated in antibiotic-mediated cell death through downstream processes (Grant et al., 2012; Lobritz et al., 2015). We hypothesize that priming respiratory metabolism by the addition of a carbon source and electron acceptor affects both target corruption and other less-characterized, downstream processes to sensitize cells to quinolones. Remarkably, one study has been able to leverage the metabolic stress induced by extreme levels of intracellular fumarate accumulation to promote a broad range of persistence phenotypes (Kim et al., 2016). This work emphasizes the complex interaction between cellular metabolic activity and drug sensitivity.

While previous starvation models have focused on the availability of carbon and nitrogen nutrients in the media (Allison et al., 2011; Amato et al., 2013; Meylan et al., 2017; Nguyen et al., 2011; Shan et al., 2017), we found that high-density static cultures quickly utilize the available dissolved oxygen, rendering this factor limiting in the metabolic process of cellular respiration. By coupling these measurements to expression data of genes that typify the aero-anaerobic transition, cyoA and frdA, we suspect that oxygen becomes limiting in both aerated and static cultures before entry into stationary phase. In our aerated cultivation system with *E. coli*, we detect an increase in persistence to ciprofloxacin when the population reached 1e8 cells per mL of media (OD600 of 0.3), or approximately 10% of the maximal carrying capacity. This is consistent with a well-described change in the growth status of cells in LB media (Sezonov et al., 2007). These findings, combined with the knowledge that the bactericidal activity of drugs such as quinolones is sensitive to the aero-anaerobic transition (Lewin et al., 1991), suggest the importance of both experimental growth conditions and sample handling in assessment of antibiotic sensitivity. Variation of growth conditions applied among laboratories could impact conclusions made in the field of antimicrobial research. We propose that the percent maximal carrying capacity be considered in order to help standardize antibiotic activity assessment.

Antibiotics from the quinolone family are a significant component of the arsenal against bacterial infectious diseases. However, a single nucleotide polymorphism within one of the gyrase subunits can increase the MIC of quinolones by orders of magnitude (Levy et al., 2004). It is important to note that persistence displayed by high cell-density populations could also be subject to selection through adaptive mutagenesis (Laureti et al., 2013). Thus, it is critical that we more thoroughly understand the mechanistic underpinnings of antibiotic persistence, so that rational approaches to the deployment of our antibiotic arsenal can be achieved (Smith and Romesberg, 2007).

Materials and Methods

The strains used for this study were *E. coli* K12 strain MG1655, *S. aureus* strain ATCC 25923 and *M. smegmatis* strain mc$^2$ 155. *E. coli* MG1655 was provided by the *E. coli* Genetic Stock Center database. *S. aureus* was provided by ATCC. *M. smegmatis* was provided by Deborah Hung's lab. *E. coli* and *S. aureus* were grown in Luria Broth (LB, Difco) medium and MOPS EZ Rich (MOPS, Teknova) medium supplemented with 0.2% glucose. *M. smegmatis* was grown in Middlebrook 7H9 supplemented with 0.05% oleic acid, 2% dextrose, and 0.004% catalase (OADC). All cells were grown at 37° C.

Chemical Preparation

Antibiotics stock solutions were made as follows: ciprofloxacin was dissolved to 10 mg/mL in 0.1M NaOH, levofloxacin was dissolved in glacial acetic acid, gentamicin, ampicillin and moxifloxacin were dissolved to 10 mg/mL in water. All metabolites were dissolved in water to the following stock solutions: 40% w/v glucose, 20% w/v fumarate, 1 M potassium nitrate.

Knockout Construction

*E. coli* genetic knockouts ΔrecB and ΔfrdA were constructed by P1 transduction from the Keio collection. Knockout strains were checked for accuracy by PCR amplification and gel electrophoresis.

Plasmid Construction

The pZE21 backbone was used for construction of all plasmids (Table 1). The kan cassette in the pZE21 was replaced with the Cm$^R$ cassette flanked by FRT sites from the pKD3 vector. The frdA promoter replaced the tet promoter through the xhoI and kpnI cut sites. The mcherry gene was replaced by frdA using the kpnI and hindIII cut sites. These plasmids were selected by 35 μg/mL chloramphenicol. The P1::rrnb-gfp plasmid was made directly from the pZE21-mcherry backbone and selected on 50 μg/mL kanamycin. Plasmids were transformed into background strains using CaCl$_2$ transformation.

Density-Persistence Assay

An overnight culture of *E. coli* was diluted 1/10,000 in MOPS or LB in either (a) a non-baffled flask in the shaking incubator, 37° C., 300 rpm (shaking condition), or (b) in 30 mL in a 100 mL bottle in a 37° C. water bath (static condition). At varying time points throughout growth, 1 mL of cells were moved to a culture tube and treated with 1 μg/mL ciprofloxacin added by pipetting; the tubes were placed in shaking or static conditions, respectively. At each time point, cells were also serially diluted in PBS and plated on LB agar plates to determine the CFU/mL at the time of treatment. Time points were taken until cells reached maximum carrying capacity. After 24 hours of treatment, 100 μl of cells from each tube was spun down and re-suspended in PBS on a 96-well plate. Cells were then serially diluted and plated on LB agar plates. The CFU/mL at treatment was normalized by the CFU/mL of stationary phase cells (% max CFU/ml).

Potentiation Assays

Cells were grown for 24 hours in either (a) a non-baffled flask overnight in the shaking incubator, 37° C., 300 rpm (shaking condition), or (b) in 30 mL in a 100 mL bottle in a 37° C. water bath (static condition). For the shaking condition, the volume of culture was set to a tenth of the flask volume. For potentiation via metabolites, 1 mL of culture was allocated to 14 mL culture tubes and treated with varying concentrations of ciprofloxacin, sugars and electron acceptors. After 24 hours of treatment, 100 μl of cells were spun down for 5 min at 3500 rpm in a 96-well plate. Cells were re-suspended in PBS and serially diluted in PBS by 10-fold. *E. coli* and *S. aureus* were spotted on LB Agar (Difco) plates; *M. smegmatis* was spotted on 7H10(Difco)+ 10% v/v OADC supplement (Hardy Diagnostics) plates. The plates were incubated at 37° C. and colonies were counted, reported as colony-forming units per mL (CFU/ml). For potentiation with oxygen, filtered air was bubbled (10 psi) into cells grown in the static condition for 24 H hours with or without glucose. These cells were then spun down and resuspended in PBS, serially diluted and plated on LB Agar plates.

Dilution Assay

An overnight culture of *E. coli* was diluted 1/10, 1/100, 1/1000, and 1/10000 in non-baffled flasks. The cultures were grown for 1 h and treated with either 1 μg/mL or 10 μg/mL ciprofloxacin for 24 hours. Cells were spun down and re-suspended in PBS, diluted and plated on LB agar plates to determine CFU/ml.

Fluorescent Reporter Measurements

Fluorescence was measured by a SpectraMax M3 Microplate Reader spectrophotometer (Molecular Devices). For P1::rrnb-gfp signal, an overnight culture of cells was diluted 1/10,000 in MOPS or LB containing 50 μg/mL kanamycin. At appropriate time points during growth, 300 μl of cells were moved to a black 96-well plate with clear bottom. The GFP signal was read on the plate reader at an emission/excitation of 488/510 and PMT of 20. At each time point, cells were also serially diluted and plated for CFU/mL determination.

Oxygen Probe Measurements

Dissolved oxygen in the media was measured using a Mettler Toledo InPro O2 sensor, 68601. The probe was kept in a static culture of cells in a water bath and the probe measured the percent of dissolved oxygen every five minutes.

qPCR

Bacterial pellets were collected and stored using RNAprotect (Qiagen) according to the manufacturer's instructions, and RNA was isolated using the RNeasy RNA isolation kit (Qiagen). RNA was DNAse treated and reverse transcribed with random hexamers using the Verso RT kit (Thermo Fisher Scientific). DNA contamination was tested by PCR of the RNA prep using the qPCR primers. Relative gene expression was determined using SYBR Green 1 based real time PCR (Roche). Concentrations were calculated from the linear standard curve and all transcripts were normalized to the zwf gene expression.

Ciprofloxacin Uptake Measurements

The protocol was adapted from (Asuquo and Piddock, 1993). 1 mL of Stationary phase cells was treated with ciprofloxacin and glucose-fumarate at 0.2% for 30 min. Cells were then washed 2 times in 2 mL ice cold PBS. Ciprofloxacin was extracted using 1 mL of glycine-HCl buffer at PH3 for 2 H. Cell residues were pelleted by centrifugation and fluorescence was read from the supernatant at 275 nm excitation and 410 nm emission. The quantity of ciprofloxacin was estimated using ciprofloxacin at defined concentration diluted in glycine-HCl extract from a ciprofloxacin non-treated culture.

Quantification and Statistical Analysis

All graphics and statistical analyses were done using PRISM software version 7. FIG. 1E the comparison between WT and the ppGpp$^0$ was tested using two-tailed Mann-Whitney P=0.017 n=5 ppGpp$^0$ and n=7 for WT. FIGS. 2D and 2E, comparison to the 120 min time point was using Two tailed unpaired T-test; FIG. 2D all significant value: P-value<0.001. FIG. 2E all significant value: P-value<0.05

TABLE 1

Reagents Table

| REAGENT or RESOURCE | SOURCE | IDENTIFIER |
|---|---|---|
| *Bacterial and Virus Strains* | | |
| *Escherichia coli* MG1655 | *E. coli* Genetic Stock Center | CGSC# 6300 |
| *Escherichia coli* ECOM: ΔcydAB ΔcyoABCD ΔcbdAB ΔygiN | (Portnoy et al., 2008) | ECOM4LA |
| *Staphylococcus aureus* | ATCC | 25923 |
| *Mycobacterium smegmatis* MC2 155 | Hung lab | MC$^2$155 |
| MG1655 ΔfrdA | this paper | N/A |
| MG1655 ΔfrdA ΔfrdA::frdA-cat | this paper | N/A |
| MG1655 ΔrelAΔspoT | (Mathieu et al., 2016) | N/A |
| *Chemicals, Peptides, and Recombinant Proteins* | | |
| LB Broth | Difco | Lot #5202513 |
| MOPS media | Technova | |
| 7H10 media | Difco | Lot #5097702 |
| Ciprofloxacin | Sigma | #17850 |
| Levofloxacin | Sigma | #28266 |
| Gentamicin | Sigma | #G1264 |
| Ampicillin | Sigma | #A9518 |
| Moxifloxacin | Sigma | #SML1581 |
| Glucose | Fisher scientific | #D16 |
| Fumarate | Sigma | #F1506 |
| Potassium nitrate | Sigma | #P8394 |
| DMSO | ThermoFisher | #85190 |
| *Oligonucleotides* | | |
| cyoA forward primer for QPCR: GGTACTTCCAGGCGAAACCA | This paper | N/A |
| cyoA reverse primer for QPCR: TTGGTCTGGAGCAACGTTCA | This paper | N/A |
| frdA forward primer for QPCR: TACGTTGACGCTACCATCCG | This paper | N/A |
| frdA reverse primer for QPCR: TATTTCGTCCACCACTGCCC | This paper | N/A |
| zwf forward primer for QPCR: TGCCGCTTTATCCCAGTCAG | This paper | N/A |
| zwf reverse primer for QPCR: GCGTCGTAAATTGCTGCCTT | This paper | N/A |
| Primer to clone frdA promoter into pZE backbone, forward: GATA CTCGAG ATCAAACAGCGGTGGG | This paper | N/A |
| Primer to clone frdA promoter into pZE backbone, reverse: GTAT GAATTC GACATTCCTCCAGATTGT | This paper | N/A |
| Primer to clone frdA gene into pZE backbone, forward: ctga GGTACCgtgCAAACCTTTCAAGC | This paper | N/A |
| Primer to clone frdA gene into pZE backbone, reverse: gtca ggatcc tcaGCCATTCGCCT | This paper | N/A |
| frdA forward sequencing: GTGCAAACCTTTCAAGC | This paper | N/A |
| frdA reverse sequencing: TCAGCCATTCGCCTTC | This paper | N/A |
| frdA promoter forward sequencing: ATCAAACAGCGGTGGG | This paper | N/A |
| *Recombinant DNA* | | |
| Plasmid: P1rrnB-GFP-kan | (Mathieu et al., 2016) | |
| Plasmid: PfrdA::frdA-cat | This paper | |

REFERENCES

Allison, K. R., Brynildsen, M. P., and Collins, J. J. (2011). Metabolite-enabled eradication of bacterial persisters by aminoglycosides. Nature 473, 216-220.

Amato, S. M., Orman, M. A., and Brynildsen, M. P. (2013). Metabolic control of persister formation in *Escherichia coli*. Mol Cell 50, 475-487.

Asuquo, A. E., and Piddock, L. J. (1993). Accumulation and killing kinetics of fifteen quinolones for *Escherichia coli, Staphylococcus aureus* and *Pseudomonas aeruginosa*. J Antimicrob Chemother 31, 865-880.

Balaban, N. Q., Gerdes, K., Lewis, K., and McKinney, J. D. (2013). A problem of persistence: still more questions than answers? Nat Rev Microbiol 11, 587-591.

Barraud, N., Buson, A., Jarolimek, W., and Rice, S. A. (2013). Mannitol enhances antibiotic sensitivity of persister bacteria in *Pseudomonas aeruginosa* biofilms. PLoS One 8, e84220.

Brauner, A., Fridman, O., Gefen, O., and Balaban, N. Q. (2016). Distinguishing between resistance, tolerance and persistence to antibiotic treatment. Nat Rev Microbiol 14, 320-330.

Bush, K., Courvalin, P., Dantas, G., Davies, J., Eisenstein, B., Huovinen, P., Jacoby, G. A., Kishony, R., Kreiswirth, B. N., Kutter, E., et al. (2011). Tackling antibiotic resistance. Nat Rev Microbiol 9, 894-896.

Caspi, R., Billington, R., Ferrer, L., Foerster, H., Fulcher, C. A., Keseler, I. M., Kothari, A., Krummenacker, M., Latendresse, M., Mueller, L. A., et al. (2016). The MetaCyc database of metabolic pathways and enzymes and the BioCyc collection of pathway/genome databases. Nucleic Acids Res 44, D471-480.

Conlon, B. P., Rowe, S. E., Gandt, A. B., Nuxoll, A. S., Donegan, N. P., Zalis, E. A., Clair, G., Adkins, J. N., Cheung, A. L., and Lewis, K. (2016). Persister formation in *Staphylococcus aureus* is associated with ATP depletion. Nat Microbiol 1, 16051.

Don, T., Lewis, K., and Vulic, M. (2009). SOS response induces persistence to fluoroquinolones in *Escherichia coli*. PLoS Genet 5, e1000760.

Don, T., Vulic, M., and Lewis, K. (2010). Ciprofloxacin causes persister formation by inducing the TisB toxin in *Escherichia coli*. PLoS Biol 8, e1000317.

Drlica, K., Malik, M., Kerns, R. J., and Zhao, X. (2008). Quinolone-mediated bacterial death. Antimicrob Agents Chemother 52, 385-392.

Dwyer, D. J., Belenky, P. A., Yang, J. H., MacDonald, I. C., Martell, J. D., Takahashi, N., Chan, C. T., Lobritz, M. A., Braff, D., Schwarz, E. G., et al. (2014). Antibiotics induce redox-related physiological alterations as part of their lethality. Proc Natl Acad Sci USA 111, E2100-2109.

Dwyer, D. J., Collins, J. J., and Walker, G. C. (2015). Unraveling the physiological complexities of antibiotic lethality. Annu Rev Pharmacol Toxicol 55, 313-332.

Fauvart, M., De Groote, V. N., and Michiels, J. (2011). Role of persister cells in chronic infections: clinical relevance and perspectives on anti-persister therapies. J Med Microbiol 60, 699-709.

Fuchs, S., Pane-Farre, J., Kohler, C., Hecker, M., and Engelmann, S. (2007). Anaerobic gene expression in *Staphylococcus aureus*. J Bacteriol 189, 4275-4289.

Grant, S. S., Kaufmann, B. B., Chand, N. S., Haseley, N., and Hung, D. T. (2012). Eradication of bacterial persisters with antibiotic-generated hydroxyl radicals. Proc Natl Acad Sci USA 109, 12147-12152.

Gutierrez-Estrada, A., Ramirez-Santos, J., and Gomez-Eichelmann Mdel, C. (2014). Role of chaperones and ATP synthase in DNA gyrase reactivation in *Escherichia coli* stationary-phase cells after nutrient addition. Springerplus 3, 656.

Harms, A., Maisonneuve, E., and Gerdes, K. (2016). Mechanisms of bacterial persistence during stress and antibiotic exposure. Science 354.

Kim, J. S., Cho, D. H., Heo, P., Jung, S. C., Park, M., Oh, E. J., Sung, J., Kim, P. J., Lee, S. C., Lee, D. H., et al. (2016). Fumarate-Mediated Persistence of *Escherichia coli* against Antibiotics. Antimicrob Agents Chemother 60, 2232-2240.

Knudsen, G. M., Ng, Y., and Gram, L. (2013). Survival of bactericidal antibiotic treatment by a persister subpopulation of *Listeria monocytogenes*. Appl Environ Microbiol 79, 7390-7397.

Laureti, L., Matic, I., and Gutierrez, A. (2013). Bacterial Responses and Genome Instability Induced by Subinhibitory Concentrations of Antibiotics. Antibiotics (Basel) 2, 100-114.

Levin-Reisman, I., and Balaban, N. Q. (2016). Quantitative Measurements of Type I and Type II Persisters Using ScanLag. Methods Mol Biol 1333, 75-81.

Levin-Reisman, I., Ronin, I., Gefen, O., Braniss, I., Shoresh, N., and Balaban, N. Q. (2017). Antibiotic tolerance facilitates the evolution of resistance. Science 355, 826-830.

Levy, D. D., Sharma, B., and Cebula, T. A. (2004). Single-nucleotide polymorphism mutation spectra and resistance to quinolones in *Salmonella enterica* serovar *Enteritidis* with a mutator phenotype. Antimicrob Agents Chemother 48, 2355-2363.

Lewin, C. S., Morrissey, I., and Smith, J. T. (1991). The mode of action of quinolones: the paradox in activity of low and high concentrations and activity in the anaerobic environment. Eur J Clin Microbiol Infect Dis 10, 240-248.

Lobritz, M. A., Belenky, P., Porter, C. B., Gutierrez, A., Yang, J. H., Schwarz, E. G., Dwyer, D. J., Khalil, A. S., and Collins, J. J. (2015). Antibiotic efficacy is linked to bacterial cellular respiration. Proc Natl Acad Sci USA 112, 8173-8180.

Losen, M., Frolich, B., Pohl, M., and Buchs, J. (2004). Effect of oxygen limitation and medium composition on *Escherichia coli* fermentation in shake-flask cultures. Biotechnol Prog 20, 1062-1068.

Maisonneuve, E., Castro-Camargo, M., and Gerdes, K. (2013). (p)ppGpp controls bacterial persistence by stochastic induction of toxin-antitoxin activity. Cell 154, 1140-1150.

Mathieu, A., Fleurier, S., Frenoy, A., Dairou, J., Bredeche, M. F., Sanchez-Vizuete, P., Song, X., and Matic, I. (2016). Discovery and Function of a General Core Hormetic Stress Response in *E. coli* Induced by Sublethal Concentrations of Antibiotics. Cell Rep 17, 46-57.

Meylan, S., Porter, C. B., Yang, J. H., Belenky, P., Gutierrez, A., Lobritz, M. A., Park, J., Kim, S. H., Moskowitz, S. M., and Collins, J. J. (2017). Carbon Sources Tune Antibiotic Susceptibility in *Pseudomonas aeruginosa* via Tricarboxylic Acid Cycle Control. Cell Chem Biol 24, 195-206.

Moyed, H. S., and Bertrand, K. P. (1983). hipA, a newly recognized gene of *Escherichia coli* K-12 that affects frequency of persistence after inhibition of murein synthesis. J Bacteriol 155, 768-775.

Nguyen, D., Joshi-Datar, A., Lepine, F., Bauerle, E., Olakanmi, O., Beer, K., McKay, G., Siehnel, R., Schafhauser, J., Wang, Y., et al. (2011). Active starvation responses mediate antibiotic tolerance in biofilms and nutrient-limited bacteria. Science 334, 982-986.

Paul, B. J., Ross, W., Gaal, T., and Gourse, R. L. (2004). rRNA transcription in *Escherichia coli*. Annu Rev Genet 38, 749-770.

Peng, B., Su, Y. B., Li, H., Han, Y., Guo, C., Tian, Y. M., and Peng, X. X. (2015). Exogenous alanine and/or glucose plus kanamycin kills antibiotic-resistant bacteria. Cell Metab 21, 249-261.

Portnoy, V. A., Herrgard, M. J., and Palsson, B. O. (2008). Aerobic fermentation of D-glucose by an evolved cytochrome oxidase-deficient *Escherichia coli* strain. Appl Environ Microbiol 74, 7561-7569.

Prax, M., Mechler, L., Weidenmaier, C., and Bertram, R. (2016). Glucose Augments Killing Efficiency of Daptomycin Challenged *Staphylococcus aureus* Persisters. PLoS One 11, e0150907.

Sezonov, G., Joseleau-Petit, D., and D'Ari, R. (2007). *Escherichia coli* physiology in Luria-Bertani broth. J Bacteriol 189, 8746-8749.

Shan, Y., Brown Gandt, A., Rowe, S. E., Deisinger, J. P., Conlon, B. P., and Lewis, K. (2017). ATP-Dependent Persister Formation in *Escherichia coli*. MBio 8.

Smith, P. A., and Romesberg, F. E. (2007). Combating bacteria and drug resistance by inhibiting mechanisms of persistence and adaptation. Nat Chem Biol 3, 549-556.

Tseng, C. P., Albrecht, J., and Gunsalus, R. P. (1996). Effect of microaerophilic cell growth conditions on expression of the aerobic (cyoABCDE and cydAB) and anaerobic (narGHJI, frdABCD, and dmsABC) respiratory pathway genes in *Escherichia coli*. J Bacteriol 178, 1094-1098.

Van den Bergh, B., Fauvart, M., and Michiels, J. (2017). Formation, physiology, ecology, evolution and clinical importance of bacterial persisters. FEMS Microbiol Rev 41, 219-251.

Zeiler, H. J. (1985). Evaluation of the in vitro bactericidal action of ciprofloxacin on cells of *Escherichia coli* in the logarithmic and stationary phases of growth. Antimicrob Agents Chemother 28, 524-527.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A pharmaceutical composition comprising (i) a quinolone antibiotic, (ii) 0.1-0.5% (w/v) of a carbon source selected from furanose sugars and pyranose sugars, and (iii) an electron acceptor selected from oxygen and 0.1-0.4% (w/v) fumarate.

2. The pharmaceutical composition of claim 1, wherein the quinolone antibiotic is flumequine, oxolinic acid, or rosoxacin.

3. The pharmaceutical composition of claim 1, wherein the quinolone antibiotic is a fluoroquinolone.

4. The pharmaceutical composition of claim 3, wherein the fluoroquinolone is ciprofloxacin, levofloxacin, moxifloxacin, garenoxacin, gatifloxacin, gemifloxacin, fleroxacin, lomefloxacin, nadifloxacin, norfloxacin, ofloxacin, pefloxacin, rufloxacin, balofloxacin, grepafloxacin, pazufloxacin, sparfloxacin, temafloxacin, tosufloxacin, clinafloxacin, sitafloxacin, prulifloxacin, trovalfloxacin, delafloxacin, or ozenoxacin.

5. The pharmaceutical composition of claim 1, wherein the composition comprises between 1 ng/mL and 1 µg/mL quinolone antibiotic.

6. The pharmaceutical composition of claim 1, wherein the carbon source is 0.1-0.5% (w/v) glucose.

7. The pharmaceutical composition of claim 6, wherein the carbon source is 0.2-0.4% (w/v) glucose.

8. The pharmaceutical composition of claim 1, wherein the electron acceptor is 0.1-0.4% (w/v) fumarate.

9. The pharmaceutical composition of claim 1, wherein the electron acceptor is oxygen.

10. The pharmaceutical composition of claim 1, wherein the composition comprises a fluoroquinolone antibiotic, 0.1-0.4% (w/v) fumarate, and 0.1-0.5% (w/v) glucose.

11. The pharmaceutical composition of claim 10, wherein the composition comprises:
    (1) ciprofloxacin, 0.1-0.4% (w/v) fumarate, and 0.1-0.5% (w/v) glucose;
    (2) levofloxacin, 0.1-0.4% (w/v) fumarate, and 0.1-0.5% (w/v) glucose; or
    (3) moxifloxacin, 0.1-0.4% (w/v) fumarate, and 0.1-0.5% (w/v) glucose.

12. The pharmaceutical composition of claim 1, wherein the composition further comprises one or more additional antibiotic agents.

13. A kit comprising a pharmaceutical composition of claim 1.

14. A method for sensitizing a microorganism to a quinolone antibiotic, the method comprising contacting the microorganism with the pharmaceutical composition of claim 1.

15. A method for preventing or reducing the density-dependent persistence (DDP) of a microorganism, the method comprising contacting a population of microorganisms comprised of one or more antibiotic persistent cells with the pharmaceutical composition of claim 1.

16. A method for preventing, reducing, or eliminating persister cells in a population of microorganisms, the method comprising contacting the cells with the pharmaceutical composition of claim 1.

17. A method for preventing and/or treating an infection in a subject in need thereof, wherein the infection is comprised of a population of microorganisms comprising one or more persister cells, the method comprising administering to the subject an effective amount of the pharmaceutical composition of claim 1.

18. The pharmaceutical composition of claim 1, wherein the electron acceptor is oxygen or 0.2-0.4% (w/v) fumarate.

19. The pharmaceutical composition of claim 1, wherein the electron acceptor is oxygen and 0.1-0.4% (w/v) fumarate.

20. The pharmaceutical composition of claim 1, wherein the electron acceptor is oxygen and 0.2-0.4% (w/v) fumarate.

21. The pharmaceutical composition of claim 1, wherein the fumarate is disodium fumarate.

22. The pharmaceutical composition of claim 1, wherein the composition comprises a fluoroquinolone antibiotic, 0.1-0.4% (w/v) disodium fumarate, and 0.1-0.5% (w/v) glucose.

23. The pharmaceutical composition of claim 22, wherein the composition comprises:
    (1) ciprofloxacin, 0.1-0.4% (w/v) disodium fumarate, and 0.1-0.5% (w/v) glucose;
    (2) levofloxacin, 0.1-0.4% (w/v) disodium fumarate, and 0.1-0.5% (w/v) glucose; or
    (3) moxifloxacin, 0.1-0.4% (w/v) disodium fumarate, and 0.1-0.5% (w/v) glucose.

* * * * *

SEQUENCE LISTING

```
<160> NUMBER OF SEQ ID NOS: 13

<210> SEQ ID NO 1
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 1
```
ggtacttcca ggcgaaacca                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 2
ttggtctgga gcaacgttca                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 3
tacgttgacg ctaccatccg                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 4
tatttcgtcc accactgccc                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 5
tgccgcttta tcccagtcag                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 6
gcgtcgtaaa ttgctgcctt                                              20

<210> SEQ ID NO 7
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 7
gatactcgag atcaaacagc ggtggg                                       26

<210> SEQ ID NO 8
<211> LENGTH: 28
<212> TYPE: DNA
<213> ORGANISM: Artificial Sequence

```
<220> FEATURE:
<223> OTHER INFORMATION: Synthetic polynucleotide

<400> SEQUENCE: 8
gtatgaattc gacattcctc cagattgt                                          28

<210> SEQ ID NO 9
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 9
ctgaggtacc gtgcaaacct ttcaagc                                           27

<210> SEQ ID NO 10
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 10
gtcaggatcc tcagccattc gcct                                              24

<210> SEQ ID NO 11
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 11
gtgcaaacct ttcaagc                                                      17

<210> SEQ ID NO 12
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 12
tcagccattc gccttc                                                       16

<210> SEQ ID NO 13
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 13
atcaaacagc ggtggg                                                       16
```